(12) United States Patent
Vergara, Jr. et al.

(10) Patent No.: US 12,183,446 B2
(45) Date of Patent: Dec. 31, 2024

(54) METHOD AND SYSTEM FOR FACILITATING MANAGEMENT OF WELLNESS OF USERS

(71) Applicants: Wilman Vergara, Jr., Gilbert, AZ (US); Nezar Dahdal, Phoenix, AZ (US)

(72) Inventors: Wilman Vergara, Jr., Gilbert, AZ (US); Nezar Dahdal, Phoenix, AZ (US)

( * ) Notice: Subject to any disclaimer, the term of this patent is extended or adjusted under 35 U.S.C. 154(b) by 844 days.

(21) Appl. No.: 17/134,225

(22) Filed: Dec. 25, 2020

(65) Prior Publication Data

US 2021/0125699 A1   Apr. 29, 2021

Related U.S. Application Data

(63) Continuation-in-part of application No. 15/927,739, filed on Mar. 21, 2018, now abandoned.

(60) Provisional application No. 62/474,759, filed on Mar. 22, 2017.

(51) Int. Cl.
| | |
|---|---|
| G16H 20/30 | (2018.01) |
| G06Q 30/0207 | (2023.01) |
| G06T 13/40 | (2011.01) |
| G06T 19/00 | (2011.01) |
| G16H 20/60 | (2018.01) |

(52) U.S. Cl.
CPC ......... G16H 20/30 (2018.01); G06Q 30/0215 (2013.01); G16H 20/60 (2018.01); G06T 13/40 (2013.01); G06T 19/006 (2013.01)

(58) Field of Classification Search
CPC ........ G16H 20/30; G16H 20/60; G16H 40/67; G06Q 30/0215; G06Q 40/08; G06T 13/40; G06T 19/006; A61B 2503/10; A61B 5/4866; A61B 5/1118; A61B 5/486; A61B 5/744; A61B 5/0022; H04L 67/535
See application file for complete search history.

(56) References Cited

U.S. PATENT DOCUMENTS

| | | | |
|---|---|---|---|
| 10,643,231 B1 * | 5/2020 | D'Andrea | G06Q 30/0235 |
| 2014/0067494 A1 * | 3/2014 | Squires | G06Q 30/0207 |
| | | | 705/14.1 |
| 2015/0038806 A1 * | 2/2015 | Kaleal, III | A61B 5/4833 |
| | | | 600/301 |
| 2017/0216675 A1 * | 8/2017 | Goslin | A63F 13/211 |
| 2017/0266531 A1 * | 9/2017 | Elford | A63B 71/0616 |

* cited by examiner

Primary Examiner — Fadi Haj Said
(74) Attorney, Agent, or Firm — Bruce A. Lev

(57) ABSTRACT

A method of facilitating management of wellness of a user. The method includes receiving a wellness goal associated with the user and an image representing the user, generating avatar data associated with the user based on the image and transmitting the avatar data to a display device associated with the user, receiving user activity data from a user device associated with the user, and generating avatar update data based on the user activity data and transmitting the avatar update data to the display device. Furthermore, two pictures of the user and their body measurements can be acquired by the display device and artificial intelligence used to generate and provide an avatar for the user. Furthermore, a step bank feature may be used to accumulate the user's steps as they exercise over time and allows them to redeem the steps earned at businesses on a network offering user financial incentive challenges.

6 Claims, 32 Drawing Sheets

METHOD AND SYSTEM FOR FACILITATING MANAGEMENT OF WELLNESS OF USERS

CROSS-REFERENCE TO RELATED APPLICATION

The present application is related to and claims priority from prior provisional application Ser. No. 62/474,759, filed Mar. 22, 2017, and prior non-provisional application Ser. No. 15/927,739, filed Mar. 21, 2018, which are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

Field of the Invention

The present invention relates generally to managing wellness. In particular, the present invention relates to a method and a system of facilitating management of wellness of users.

Goal-setting is one of the popular techniques used by users across the world to set and meet their goals. Many users set goals to maintain their wellness. Accordingly, they may set one or more of physical health goals, mental health goals, and educational goals. For example, for physical health goals, the users may try to set goals related to diets and exercise plans to achieve a certain fitness level. However, most users struggle to meet their physical health goals. Many users struggle to meet their goals due to lack of motivation, unenjoyable workouts, and lack of interaction with other users.

Accordingly, there is a need for improved systems and methods of facilitating management of wellness of users that may also overcome one or more of the abovementioned problems and/or limitations.

BRIEF SUMMARY OF THE INVENTION

This summary is provided to introduce a selection of concepts in a simplified form that are further described below in the Detailed Description. This summary is not intended to identify key features or essential features of the claimed subject matter. Nor is this summary intended to be used to limit the claimed subject matter's scope.

Disclosed is a method of facilitating management of wellness of users. The method may include receiving, using a communication device, at least one wellness goal associated with at least one user. Further, the method may include receiving, using the communication device, at least one image representing the at least one user. Further, the method may include generating, using a processing device, at least one avatar data associated with the at least one user based on the at least one image. Further, the method may include transmitting, using the communication device, the at least one avatar data to at least one display device associated with the at least one user. Further, the at least one display device may be configured to display at least one avatar based on the at least one avatar data. Further, the method may include receiving, using the communication device, at least one user activity data from at least one user device associated with the at least one user. Further, the method may include generating, using the processing device, at least one avatar update data based on the at least one user activity data. Further, the method may include transmitting, using the communication device, the at least one avatar update data to the at least one display device. Further, the at least one display device may be configured to display at least one updated avatar based on the at least one avatar update data.

According to some embodiments, a system for facilitating management of wellness of users is also provided. The system may include a communication device configured for receiving, using a communication device, at least one wellness goal associated with at least one user. Further, the communication device may also be configured for receiving at least one image representing the at least one user. Further, the communication device may also be configured for transmitting at least one avatar data to at least one display device associated with the at least one user. Further, the at least one display device may be configured to display at least one avatar based on the at least one avatar data. Further, the communication device may also be configured for receiving at least one user activity data from at least one user device associated with the at least one user. Further, the communication device may also be configured for transmitting at least one avatar update data to the at least one display device. Further, the at least one display device may be configured to display at least one updated avatar based on the at least one avatar update data. Further, the system may include a processing device configured for generating the at least one avatar data associated with the at least one user based on the at least one image. Further, the processing device may also be configured for generating the at least one avatar update data based on the at least one user activity data.

Further, a health-related data platform for a user/patient engagement may be provided. The platform may also provide and interact with web-based and mobile applications. The web-based and mobile applications may be configured to track user activity, manage the appearance of an avatar of the user, allow the user to unlock features to customize the avatar etc. Therefore, the users may be able to create their own personalized avatar that may resemble them. The avatar may be an interactive character that may motivate the user as they take their journey to a healthier lifestyle by losing weight with the user, eating foods that may be purchased in a marketplace with the points they accumulate by exercising. Accordingly, the users may be encouraged to meet their goals by providing motivation, making the workouts more enjoyable, and allowing more interaction with other users.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

Figure 1:
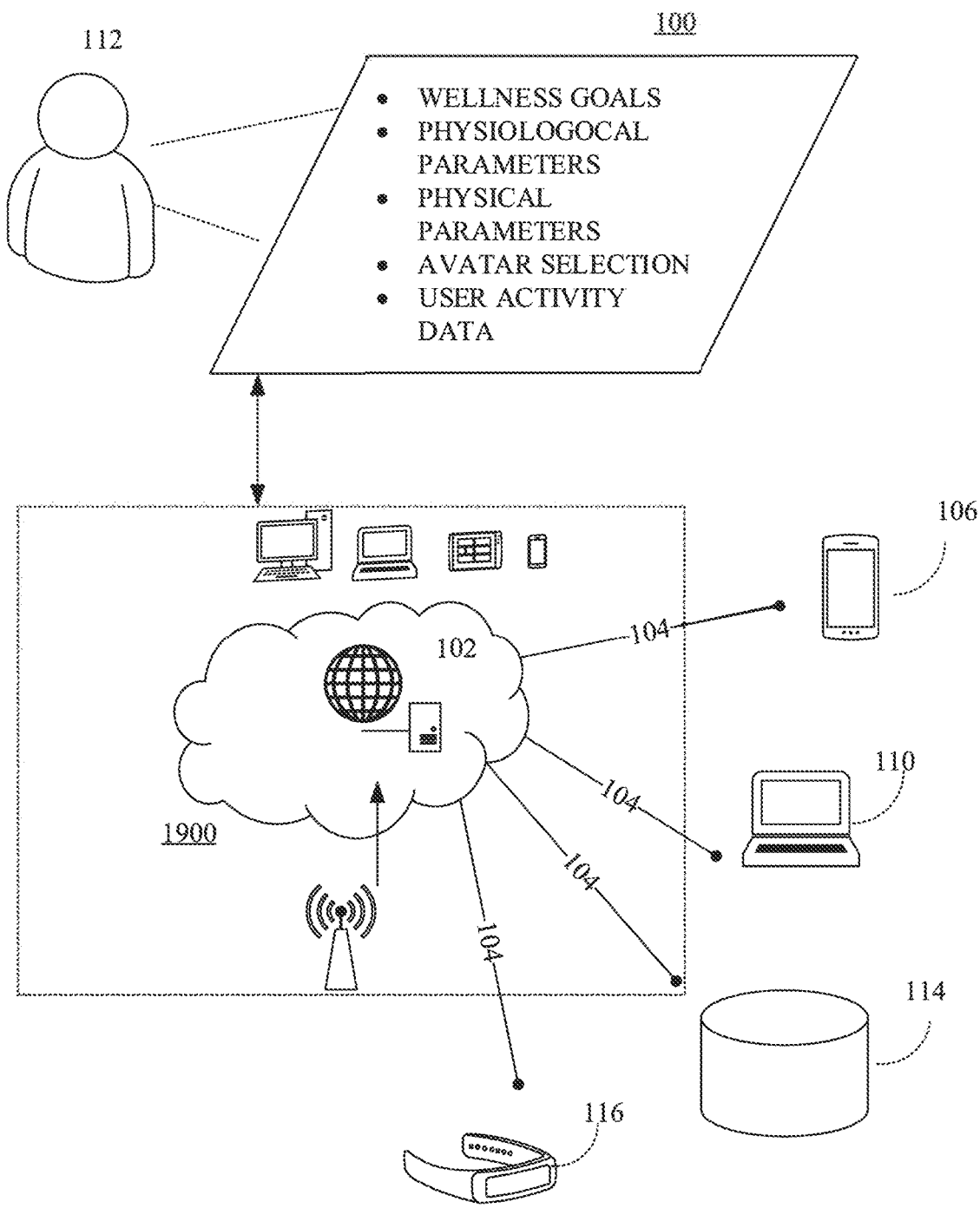
FIG. 1 is an illustration of a platform consistent with various embodiments of the present disclosure.

The various embodiments of the present invention will hereinafter be described in conjunction with the appended drawings.

DETAILED DESCRIPTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of managing wellness of users, embodiments of the present disclosure are not limited to use only in this context.

According to some embodiments, an interactive mobile platform called "KNOSIS Health" is disclosed. The platform may employ existing hardware, such as a fitness tracker to sync to the platform via an Application Program Interface (API), to engage users and collect data on the exercise and active habits of a user to leverage the data output for commercial (employer-based wellness programs), individual user (consumer) to save money on healthcare expenses, as well as educational institutions (primary, middle, secondary, and post-secondary) who wish to engage their students to living a healthier lifestyle. The platform may be used by businesses who currently offer, or may not offer, employee wellness programs as an employee engagement tool that will track, interact, as well as report an employee's activity including, but not limited to, steps, distance, running, intensity, points, location and duration through their personal fitness tracker. The employer may then apply a User Financial Incentive (UFI), at the employer's discretion, to the employee if they meet certain monthly Key Performance Indicators (KPIs) based on their activity. The employer may then leverage the data received via reports provided by the platform to reconcile it with their employer-sponsored health insurance claim data to negotiate a better health insurance contract with their current or other health insurance provider.

Further, the end users of the platform may be able to create and customize an interactive humanlike figure, known henceforth as the avatar. For example, the data output from users' fitness trackers may be used to manipulate the avatar depending on the users meeting their fitness KPIs. Furthermore, as users meet their KPIs, they may be able to unlock body parts, physical features, and accessories for the avatar that may emulate their physiology. Further, the users may be rewarded via a points system that may be redeemed in a marketplace provided by the platform. For example, the customizable portions of the avatar may include hair, torso, arms, legs, clothing, and accessories. The same avatar may be featured on the platform's homepage and an avatar page. The avatar" page may have a link where the user can enter the marketplace where the user can access and purchase items by using their points earned by meeting their KPIs.

The end users (or consumers) may download an application on their mobile device (for example, iOS™ devices and Android™ devices) from an application store for a fee. The consumer version of the application may be similar to the commercial version of the application with the exception of: reporting, employer information, and employee wellness program capabilities. Further, the platform may include contracts with various commercial health insurance plans to offer UFIs to individual users whose employer does not participate in an employee wellness program or the user has a self-funded commercial health insurance plan.

The platform may be hosted on a cloud-based server or physical, secure server. The data may be collected and stored for analysis and reporting to commercial clients (employers). A front-end data entry may include obtaining biometric and demographic information for any user, connectivity capabilities and syncing capabilities to any of the fitness trackers currently available in the market (such as FitBit, Garmin™, Apple Watch™, etc.) via their Application Program Interface (API). Further, a back-end data analysis may be performed to check if the users have met their KPIs. Further, based on the analysis a Greek God may be assigned to the user as a badge, which may be displayed on their profile. For example, if a user hits their personal milestones and reaches the pinnacle, then the Greek God "Mount Olympus" may be assigned to the user, which would indicate that the user has reached peak, optimal fitness form. Further, reward points may be awarded to the client. The accumulated points may be used to purchase items in the marketplace. Further, graphs and progress bars may be shown to a user to indicate how much they have earned in their corresponding UFI program as well as interaction with their avatar for motivational purposes.

The platform may also provide the capability to users to be able to challenge other users. The users may be able to find users within a certain distance (such as a 10-mile radius) of their location.

The platform may also have an inbox feature where partner businesses, sponsors, and other organization may send users messages containing credits, tokens, coupons, special member pricing, and other incentives of monetary value when they meet certain KPIs as well as they stay engaged in the platform for a prolonged period of time (such as greater than 180 days) as a reward for their loyalty and meeting fitness goals.

Referring now to figures, FIG. 1 is an illustration of a platform 100 consistent with various embodiments of the present disclosure. By way of non-limiting example, the online platform 100 for facilitating management of wellness of users may be hosted on a centralized server 102, such as, for example, a cloud computing service. The centralized server 102 may communicate with other network entities, such as, for example mobile devices 106 (such as a smartphone, a laptop, a tablet computer etc.), other electronic devices 110 (such as desktop computers, etc.), databases 114 (such as avatar databases, health databases), smart wristwatches 116, via a communication network 104 such as, but not limited to, the Internet. Further, users of the platform may include one or more relevant parties such as users, employers, employees of insurance companies and system administrators. Accordingly, electronic devices operated by the one or more relevant parties may be in communication with the platform 100.

A user 112, such as the one or more relevant parties, may access the platform 100 through a software application. The software application may be embodied as, for example, but not be limited to, a website, a web application, a desktop application, and a mobile application compatible with a computing device 1900. For example, the user 112 may access the platform 100 via a mobile application called "KNOSIS". The mobile application called "KNOSIS" is explained in further detail in conjunction with FIGS. 7-18 below. Further, the online platform 100 may provide an Application Program Interface (API), to engage users and collect data on the exercise and active habits of the users to leverage the data output for commercial (employer-based wellness programs), individual user (consumer) to save money on healthcare expenses, as well as educational institutions (primary, middle, secondary, and post-secondary) who wish to engage their students to living a healthier lifestyle. Further, two versions of the mobile application "KNOSIS" may be provided. The two versions may include a commercial version and a consumer version. The commercial version of the mobile application "KNOSIS" may be provided to businesses who currently offer, or may not offer, employee wellness programs as an employee engagement tool that will track, interact, as well as report an employee's activity including, but not limited to: steps, distance, running, intensity, points, location and duration through their personal fitness tracker. The consumer version may be provided to mobile application users where they may be able to download the application from an application store for a fee.

In further embodiments, the one or more wellness goals may be received from one or more user devices associated with the one or more users. For example, the one or more user devices may include mobile devices 106. In some embodiments, the one or more wellness goals may be received from one or more computing devices. For example, the one or more computing devices may include electronic devices 110. Further, the one or more computing devices may be associated with one or more organizations associated with the one or more users. For example, the one or more organizations may include a health insurance company. Further, the one or more users may be employed by the one or more organizations. Yet further, the one or more wellness goals may be stipulated by the one or more organizations. Further, the one or more computing devices may be associated with the one or more users. Yet further, the one or more wellness goals may be specified by the one or more users.

Figure 2:
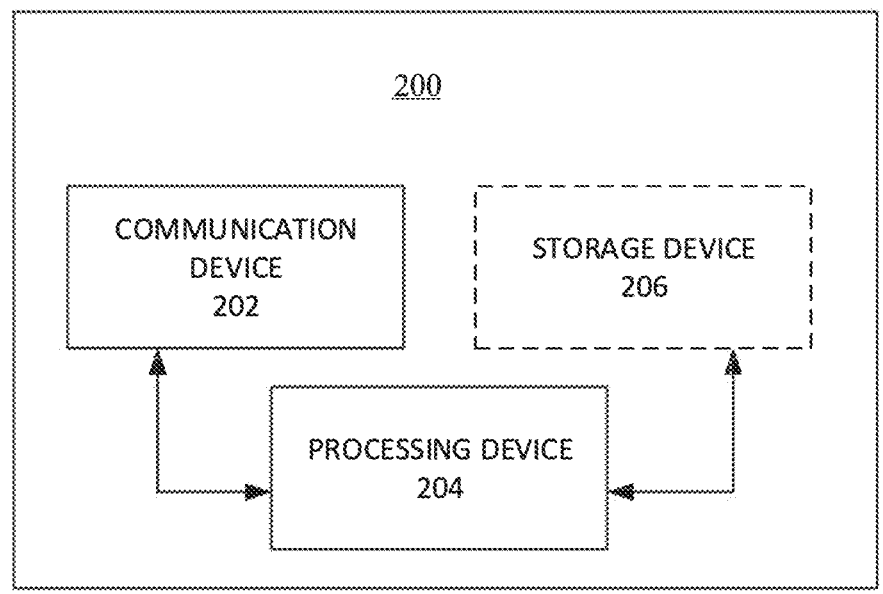
FIG. 2 is a block diagram of a system for facilitating management of wellness of users in accordance with some embodiments.

FIG. 2 is a block diagram of a system 200 for facilitating management of wellness of users in accordance with some embodiments. The system 200 may include a communication device 202 configured for receiving, using the communication device 202, and one or more wellness goals associated with one or more users. In some embodiments, the one or more wellness goals may include a physical health goal, such as, but not limited to, a weight-loss goal, a weight-gain goal, a weight-maintenance goal. In some embodiments, the one or more wellness goals may include a mental health goal, such as, but not limited to, a stress-reduction goal, an attention-enhancement goal, and a memory-enhancement goal. In some embodiments, the one or more wellness goals may include an educational goal.

Further, the communication device 202 may also be configured for receiving one or more images representing the one or more users. In some embodiments, the one or more images may be received from the one or more user devices. In some embodiments, the one or more images may be received from an image capturing device associated with the one or more users. In some embodiments, the one or more images may be received from a social network server associated with the one or more users. The one or more images may include a two-dimensional image. In some embodiments, the one or more images may include two or more two-dimensional images.

Further, the communication device 202 may also be configured for transmitting at least one avatar data to one or more display devices associated with the one or more users. In some embodiments, the at least one avatar data may include at least one of a three-dimensional image and a two-dimensional image. Further, the one or more display devices may be configured to display at least one avatar based on the at least one avatar data. In some embodiments, the at least one avatar may include a humanoid. In some embodiments, the at least one avatar may include a head portion of the humanoid.

In some embodiments, the communication device 202 may further include transmitting, using the communication device, two or more avatars to the one or more computing devices. Further, the one or more computing devices may be configured to display the two or more avatars.

In some embodiments, the communication device 202 may further include receiving, using the communication device, at least one avatar selection from one or more computing devices associated with the one or more users. Further, the at least one avatar data may be based on the at least one avatar selection.

Further, the communication device 202 may also be configured for receiving at least one user activity data from the one or more user devices. For example, the at least one user activity data may include calorie intake data, calorie expenditure data and Body Mass Index (BMI) data. The receiving at least one user activity data may be stored in a storage device 206 of the system 200. For example, the at least one user activity data may be stored using block-chain technology. In some embodiments, the one or more user devices may include one or more wearable monitoring devices configured to monitor one or more of one or more physiological variables and one or more physical variables of the one or more users. For example, one or more wearable monitoring devices may include a fitness tracking band configured to be worn around a wrist of a user. The one or more physiological variables may include one or more of body temperature, heart rate, respiratory rate, blood pressure, blood-oxygen level and blood-insulin level. The one or more physical variables may include one or more of location, distance traveled, speed, acceleration, and number of repetitive actions.

In some embodiments, the at least one user device may include a smart exercising device configured to facilitate performance of an exercise. Further, the smart exercising device may include one or more sensors configured to detect at least one exercise data associated with the exercise. Further, the smart exercising device may include a transceiver configured to transmit the at least one exercise data from the at least one sensor to the communication device. For example, the smart exercising device may include a smart treadmill, a smart dumbbell, a smart weight, a smart strength training equipment, a smart exercise ball, a smart resistance band, a smart exercise mat and a smart shoe.

In some embodiments, the one or more user devices may be configured to monitor food intake corresponding to the one or more users. In some embodiments, the one or more user devices may include one or more of a smart oven, a smart food processor and a smart refrigerator.

In some embodiments, the at least one user activity data corresponds to one or more user body parts of the one or more users. The one or more user body parts may correspond to one or more muscle groups of the one or more users. The at least one avatar update data corresponds to one or more avatar body parts associated with the one or more user body parts.

In some embodiments, the at least one avatar data may include an animation, wherein the animation may be based on the at least one user activity data. Further, the animation performed by the at least one avatar may mimic a corresponding action performed by the one or more users.

Further, the communication device 202 may also be configured for transmitting at least one avatar update data to the one or more display devices. In some embodiments, the one or more user devices may include the one or more display devices. In some embodiments, the one or more display devices may be comprised in the one or more computing devices associated with the one or more users. Further, the one or more display devices may be configured to display at least one updated avatar based on the at least one avatar update data. For example, the at least one avatar update data may include one or more of fitness improvement data and fitness deterioration data. Further, an appearance of the one or more avatar body parts (the at least one updated avatar) may be based on the at least one avatar update data.

Further, the system 200 may include a processing device 204 configured for generating the at least one avatar data associated with the one or more users based on the one or more images. Further, the processing device 204 may also be configured for generating the at least one avatar update data based on the at least one user activity data.

In some embodiments, a first computing device of the one or more computing devices may be associated with a first user. Further, a second computing device of the one or more computing devices may be associated with a second user. Further, a first wellness goal of the one or more wellness goals may be associated with the first user.

Further, the first wellness goal may be specified by the second user. Further, a second wellness goal of the one or more wellness goals may be associated with the second user. Further, the second wellness goal may be specified by the first user. Further, a first location of the first user may be within a user-determined distance of a second location of the second user.

In some embodiments, the processing device 204 may be further configured for analyzing each of the one or more wellness goals and the at least one user activity data, determining achievement of the one or more wellness goals based on the analyzing and assigning one reward to at least one user account associated with the one or more users based on the achievement of the one or more wellness goals. The one or more rewards may include one or more of a monetary reward, a product-coupon, a service-coupon, a discount voucher, digital currency.

In some embodiments, the one or more rewards may be based on one or more of a type of at least one user activity, a duration of the at least one user activity and an intensity of the at least one user activity. Further, a quantity of the one or more rewards may be based on a magnitude corresponding to the at least one user activity. For example, the at least one user activity may include physical exercising. The physical exercising may include one or more of aerobic training, strength training, balance training and flexibility training.

In some embodiments, the communication device 202 may be further configured for receiving at least one baseline data corresponding to the one or more wellness goals. The at least one baseline data may be received periodically at a predetermined time interval. Further, the processing device 204 may be further configured for comparing the at least one user activity data with the at least one baseline data. In some embodiments, the comparing may include determining a difference between the at least one user activity data and the at least one baseline data. Further, the processing device 204 may be configured for validating the at least one user activity data based on the comparing. Further, the validating may be based on the difference being less than a predetermined threshold.

Further, the communication device 202 may be configured to transmit an alert to the one or more computing devices associated with the one or more users. Further, the alert may be transmitted if the difference is greater than the predetermined threshold. For example, the alert may indicate that the at least one user activity data is received from a different user and not the user registered with the system 200.

In some embodiments, the processing device 204 may be further configured for analyzing each of the one or more wellness goals and the at least one user activity data, determining achievement of the one or more wellness goals based on the analyzing and unlocking at least one feature of the at least one avatar based on the achievement. For example, the at least one feature may include one or more of an avatar body part, an avatar accessory and an avatar clothing.

Figure 3:
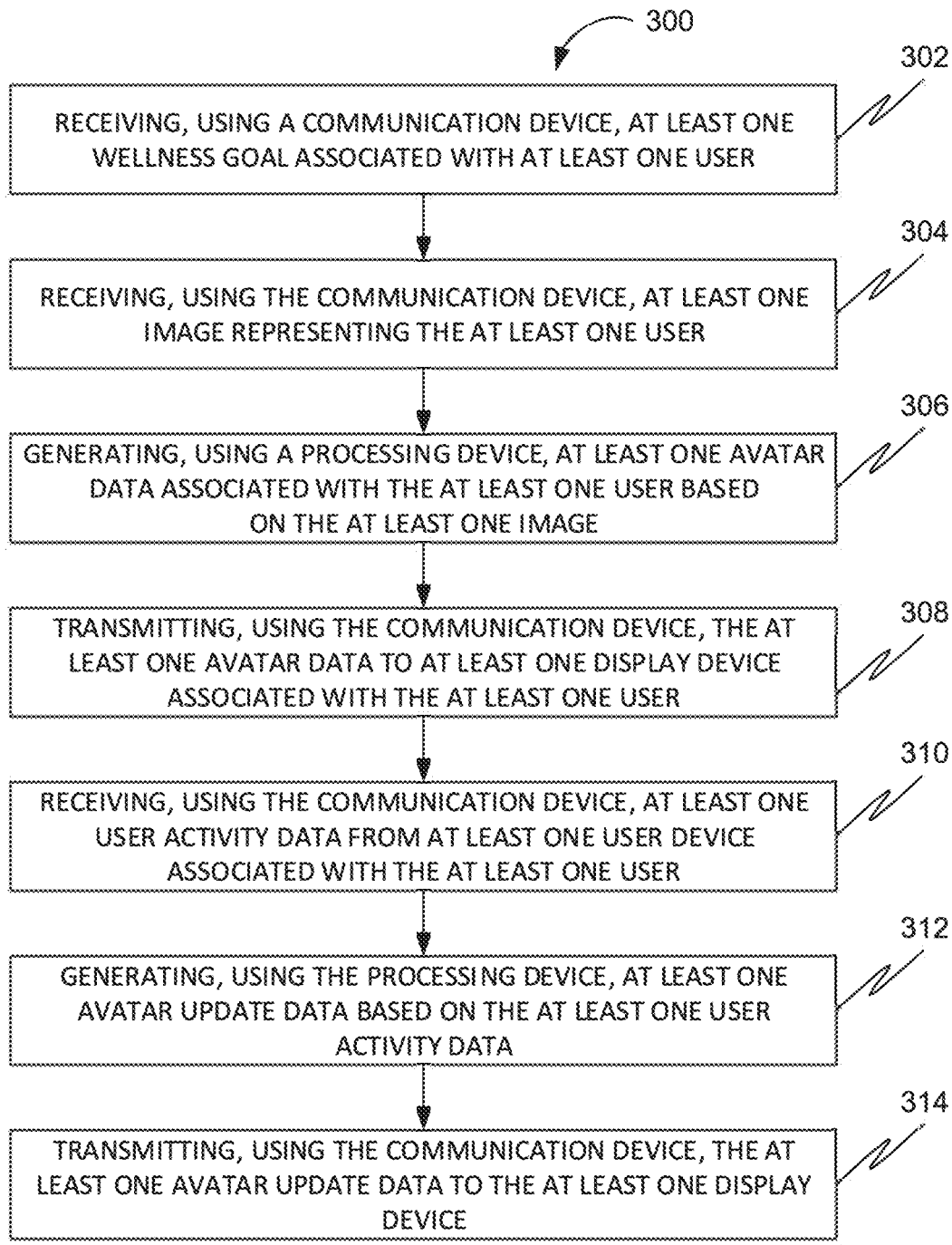
FIG. 3 is a flowchart of a method for facilitating management of wellness of users in accordance with some embodiments.

FIG. 3 is a flowchart of a method 300 for facilitating management of wellness of users in accordance with some embodiments. At 302, the method 300 may include receiving, using a communication device (such as the communication device 202), one or more wellness goals associated with one or more users. In some embodiments, the one or more wellness goals may include a physical health goal, such as, but not limited to, a weight-loss goal, a weight-gain goal, a weight-maintenance goal. In some embodiments, the one or more wellness goals may include a mental health goal, such as, but not limited to, a stress-reduction goal, an attention-enhancement goal, and a memory-enhancement goal. In some embodiments, the one or more wellness goals may include an educational goal.

Further, at 304, the method 300 may include receiving, using the communication device, one or more images representing the one or more users. In some embodiments, the one or more images may be received from the one or more user devices. In some embodiments, the one or more images may be received from an image capturing device associated with the one or more users. In some embodiments, the one or more images may be received from a social network server associated with the one or more users. The one or more images may include a two-dimensional image. In some embodiments, the one or more images may include two or more two-dimensional images.

Further, at 306, the method 300 may include generating, using a processing device (such as the processing device 204), at least one avatar data associated with the one or more users based on the one or more images.

Further, at 308, the method 300 may include transmitting, using the communication device, the at least one avatar data to one or more display devices associated with the one or more users. In some embodiments, the one or more user devices may include the one or more display devices. In some embodiments, the one or more display devices may be comprised in the one or more computing devices associated with the one or more users.

Further, the one or more display devices may be configured to display one or more avatars based on the at least one avatar data. For example, the display device may be a mobile phone of a user, wherein an avatar of the user may be displayed on the mobile phone of the user.

In some embodiments, the method 300 may further include transmitting, using the communication device, two or more avatars to the one or more computing devices. Further, the one or more computing devices may be configured to display the two or more avatars.

In further embodiments, the method 300 may further include receiving, using the communication device, one or more avatar selections from the one or more computing devices associated with the one or more users. Further, the at least one avatar data may be based on the one or more avatar selections.

Further, at 310, the method 300 may include receiving, using the communication device, at least one user activity data from the one or more user devices associated with the one or more users. For example, the at least one user activity data may include calorie intake data, calorie expenditure data and Body Mass Index (BMI) data.

Further, at 312, the method 300 may include generating, using the processing device, at least one avatar update data based on the at least one user activity data. Further, at 314, the method 300 may include transmitting, using the communication device, the at least one avatar update data to the one or more display devices. Further, the one or more display devices may be configured to display at least one updated avatar based on the at least one avatar update data.

In some embodiments, the at least one avatar data may include an animation. The animation may be based on the at least one user activity data. Further, the animation performed by the at least one avatar mimics a corresponding action performed by the one or more users.

In some embodiments, a first computing device of the one or more computing devices may be associated with a first user. Further, a second computing device of the one or more computing devices may be associated with a second user. Further, a first wellness goal of the one or more wellness goals may be associated with the first user. Further, the first wellness goal may be specified by the second user. Further, a second wellness goal of the one or more wellness goals may be associated with the second user. Further, the second wellness goal may be specified by the first user. Accordingly, the first user and the second user may challenge each other. Further, a first location of the first user may be within a user-determined distance of a second location of the second user.

Figure 4:
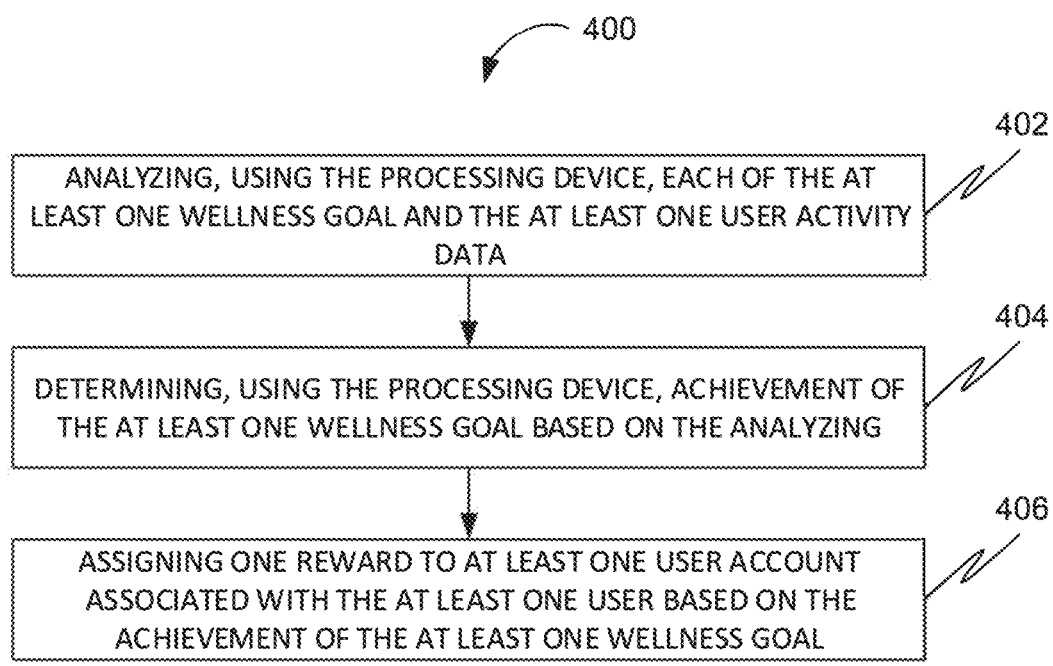
FIG. 4 is a flowchart of a method for rewarding one or more users in accordance with some embodiments.

FIG. 4 is a flowchart of a method 400 for rewarding the one or more users in accordance with some embodiments. At 402, the method 400 may include analyzing, using the processing device, each of the one or more wellness goals and the at least one user activity data of the one or more users. Further, at 404, the method 400 may include determining, using the processing device, achievement of the one or more wellness goals based on the analyzing. Yet further, at 406, the method 400 may include assigning one or more rewards to at least one user account associated with the one or more users based on the achievement of the one or more wellness goals. The one or more rewards may include one or more of a monetary reward, a product-coupon, a service-coupon, a discount voucher and digital currency.

In some embodiments, the one or more rewards may be based on one or more of a type of the at least one user activity, a duration of the at least one user activity and an intensity of the at least one user activity. Further, a quantity of the one or more rewards may be based on a magnitude corresponding to the at least one user activity. The at least one user activity may include physical exercising. Further, the physical exercising may include one or more of aerobic training, strength training, balance training and flexibility training. Further, the method 400 may include storing, using a storage device (such as the storage device 206), the at least one user activity data using block-chain technology.

Figure 5:
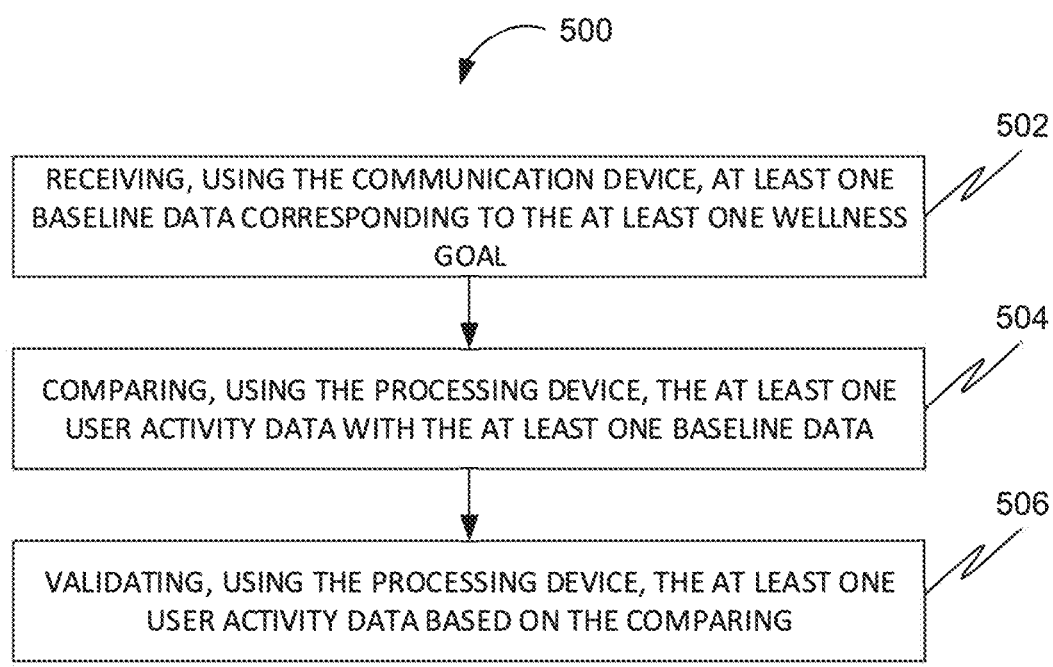
FIG. 5 is a flowchart of a method for validating at least one user activity data in accordance with some embodiments.

FIG. 5 is a flowchart of a method 500 for validating the at least one user activity data in accordance with some embodiments. At 502, the method 500 may include receiving, using the communication device, at least one baseline data corresponding to the one or more wellness goals. In some embodiments, the at least one baseline data may be received periodically at a predetermined time interval. Further, at 504, the method 500 may include comparing, using the processing device, the at least one user activity data with the at least one baseline data. Yet further, at 506, the method 500 may include validating, using the processing device, the at least one user activity data based on the comparing.

In some embodiments, the comparing (at 504) may include determining a difference between the at least one user activity data and the at least one baseline data. Further, the validating (at 506) may be based on the difference being less than a predetermined threshold.

In some embodiments, the method 500 may further include transmitting, using the communication device, an alert to one or more computing devices associated with the one or more users when the difference may be greater than the predetermined threshold. The alert may indicate that the at least one user activity data is received from a different user.

Figure 6:
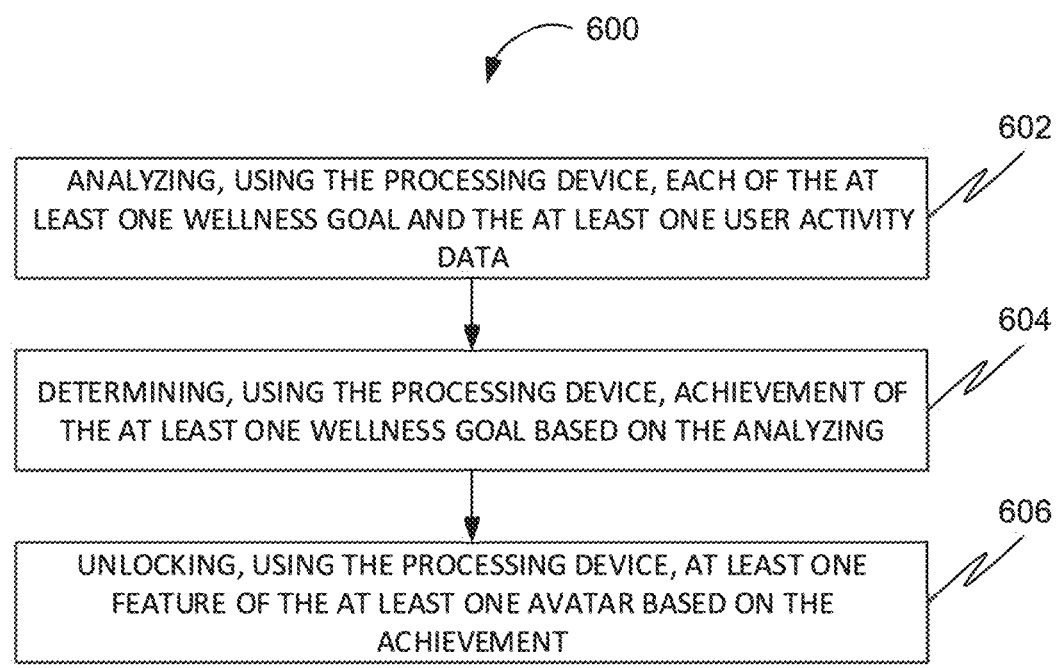
FIG. 6 is a flowchart of a method for unlocking one or more features of one or more avatars in accordance with some embodiments.

FIG. 6 is a flowchart of a method 600 for unlocking one or more features of the one or more avatars in accordance with some embodiments. At 602, the method 600 may include analyzing, using the processing device, each of the one or more wellness goals and the at least one user activity data. At 604, the method 600 may include determining, using the processing device, achievement of the one or more wellness goals based on the analyzing. At 606, the method 600 may include unlocking, using the processing device, the one or more features of the one or more avatars based on the achievement. For example, the one or more features may include one or more of an avatar body part, an avatar accessory and an avatar clothing.

Figure 7:
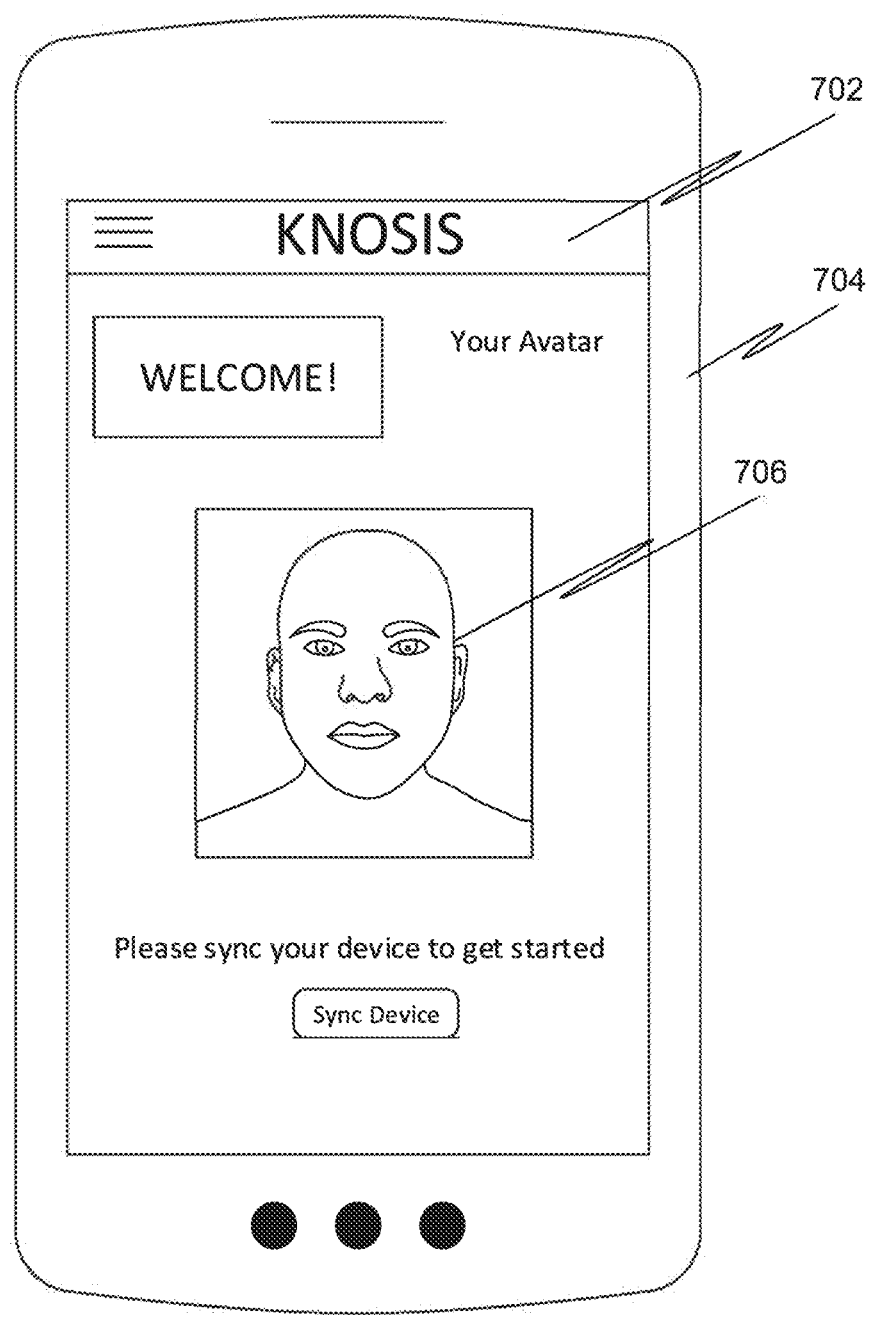
FIG. 7 is a user interface of a mobile application displaying an avatar, in accordance with an exemplary embodiment.

FIG. 7 is a user interface 702 of the mobile application "KNOSIS" installed on the user device 704 displaying an avatar 706, in accordance with an exemplary embodiment. In some embodiments, the one or more avatars may include a humanoid. Further, the one or more avatars may include a head portion of the humanoid. The avatar 706 includes a head portion of a humanoid.

Figure 8:
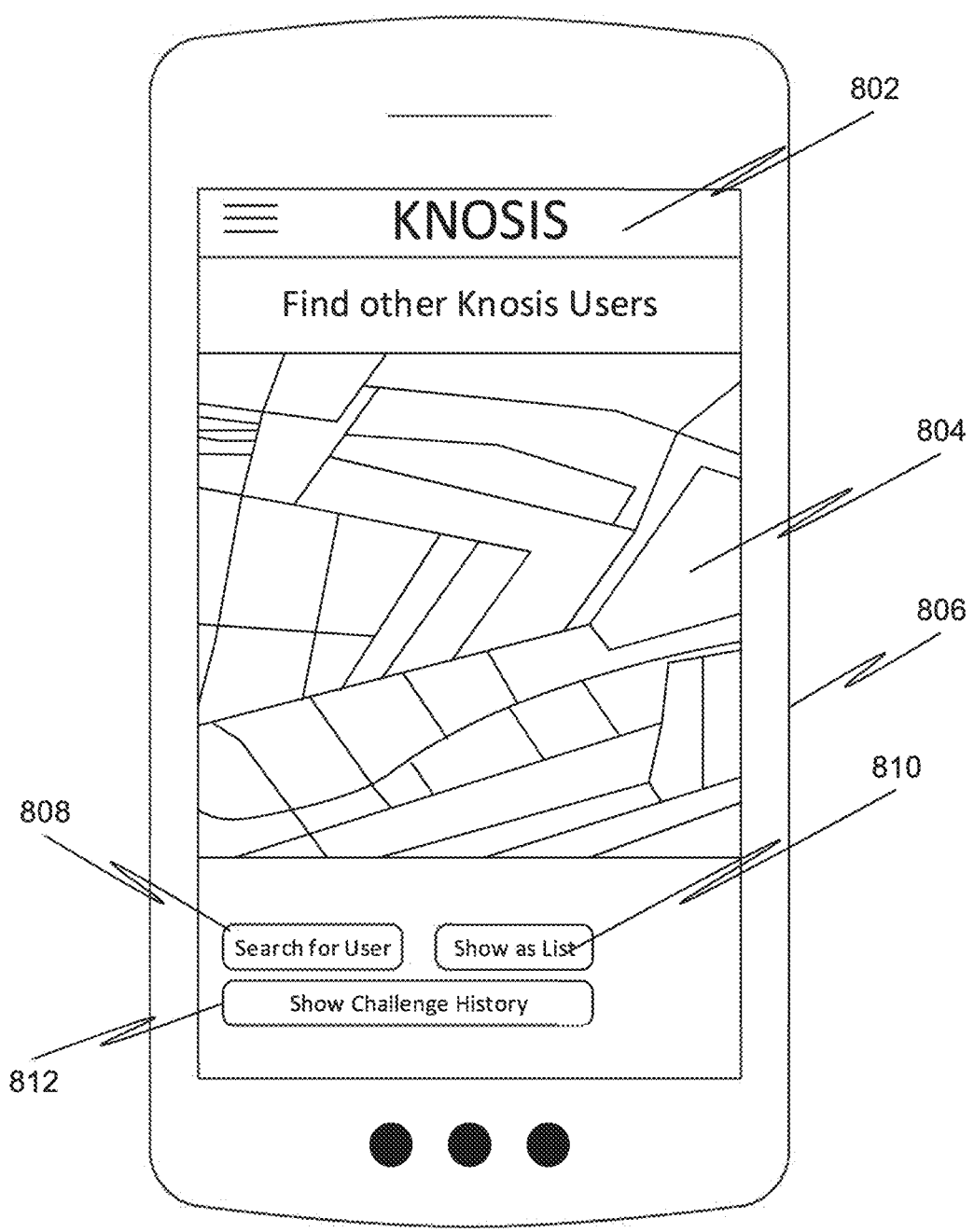
FIG. 8 is a user interface of the mobile application displaying a map, in accordance with an exemplary embodiment.

FIG. 8 is a user interface 802 of the mobile application "KNOSIS" displaying a map 804 (such as, a map provided by Google Maps™), in accordance with an exemplary embodiment. The map 804 may be displayed on the user device 806 of the first user. The map 804 may display the users within the user-determined distance from the first user. For example, the user-determined distance may be 10 miles. The user interface 802 may also include a "Search for User" button 808, a "Show as List" button 810, and a "Show Challenge History" button 812. If the first user selects the "Show as List" button 810, then the mobile application "KNOSIS" displays a user interface 902 shown in FIG. 9.

Figure 9:
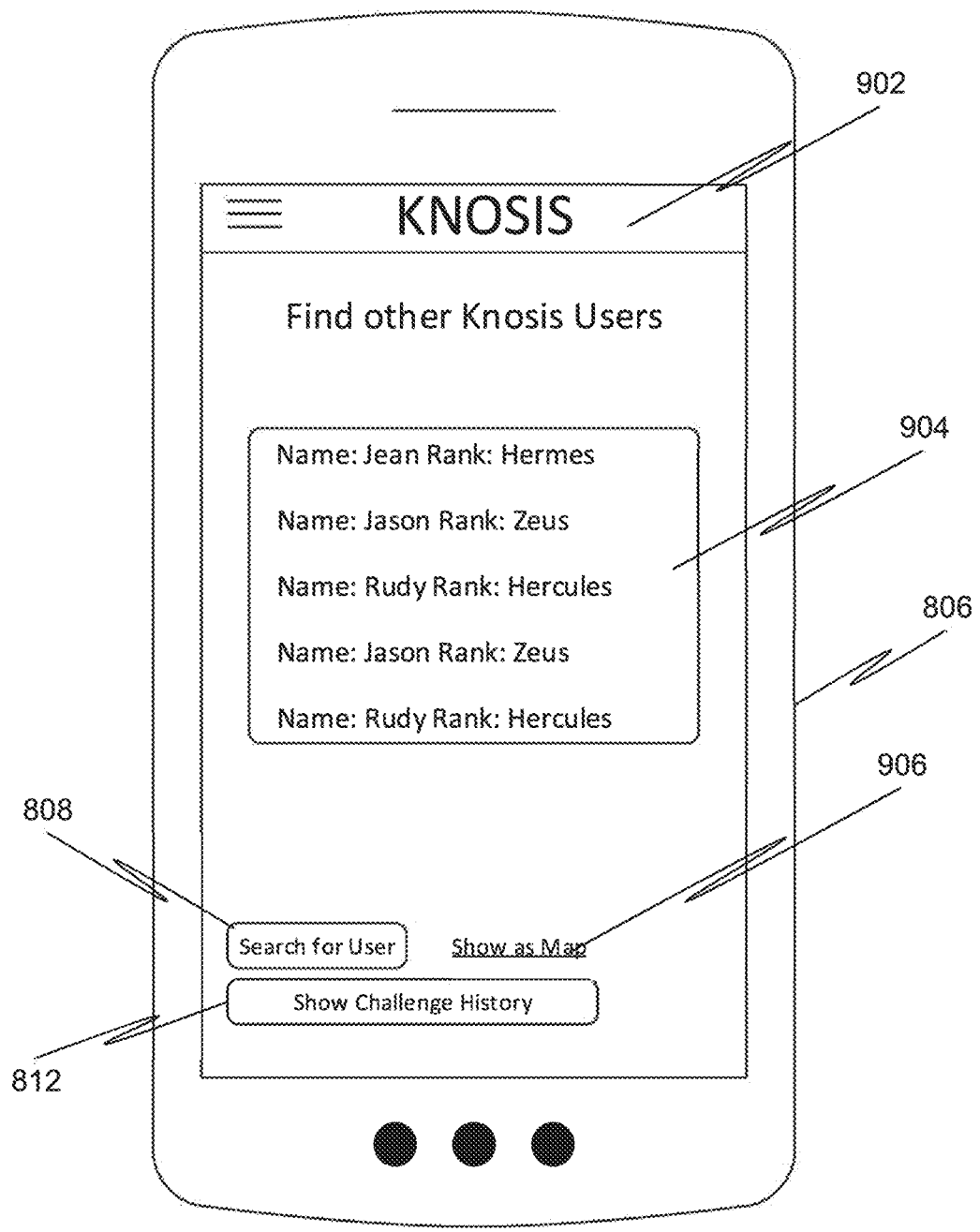
FIG. 9 is a user interface of the mobile application showing a list of the users, in accordance with an exemplary embodiment.

As shown in FIG. 9, the user interface 902 includes a list of the users 904 within a user-determined distance from the first location of the first user. Further, the user interface 902 includes a "Show as Map" button 906. If the first user selects the "Show as Map" button 906, then, the mobile application "KNOSIS" displays the user interface 802. Further, if the first user selects the "Show Challenge History" button 812, then, the mobile application "KNOSIS" displays the user interface 1002 shown in FIG. 10.

Figure 10:
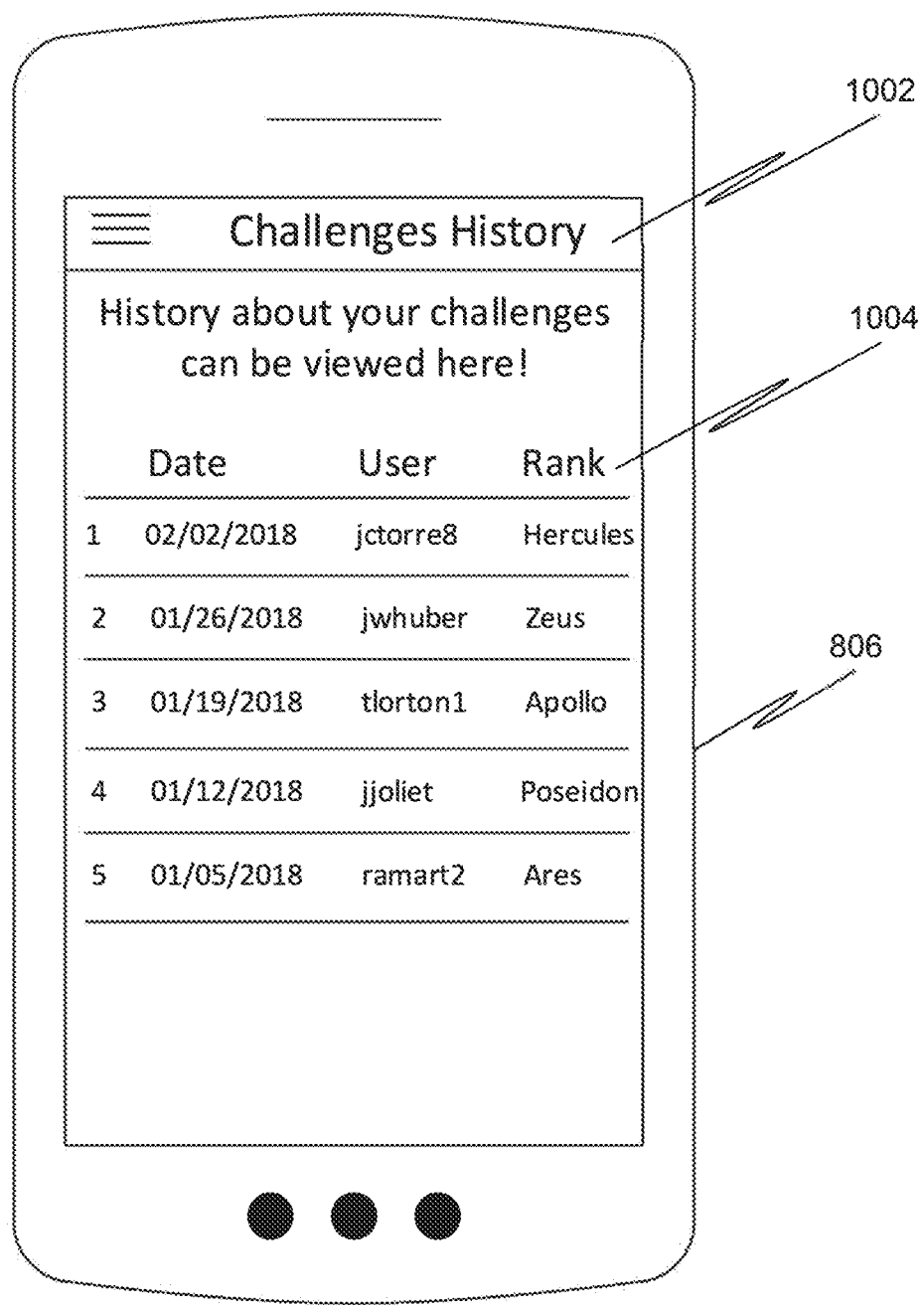
FIG. 10 is a user interface of the mobile application showing a table related to a challenge history, in accordance with an exemplary embodiment.

As shown in FIG. 10, the user interface 1002 includes a table 1004 with three columns date, user and rank. The table 1004 includes details about the previous challenges that the first user has participated in.

In further embodiments, the one or more users may participate in group sessions. For example, the group sessions may be live streamed group training sessions, which may help the one or more users meet their one or more wellness goals. If the first user participates in a group session, the mobile application "KNOSIS" displays the user interface 1102 shown in FIG. 11.

Figure 11:
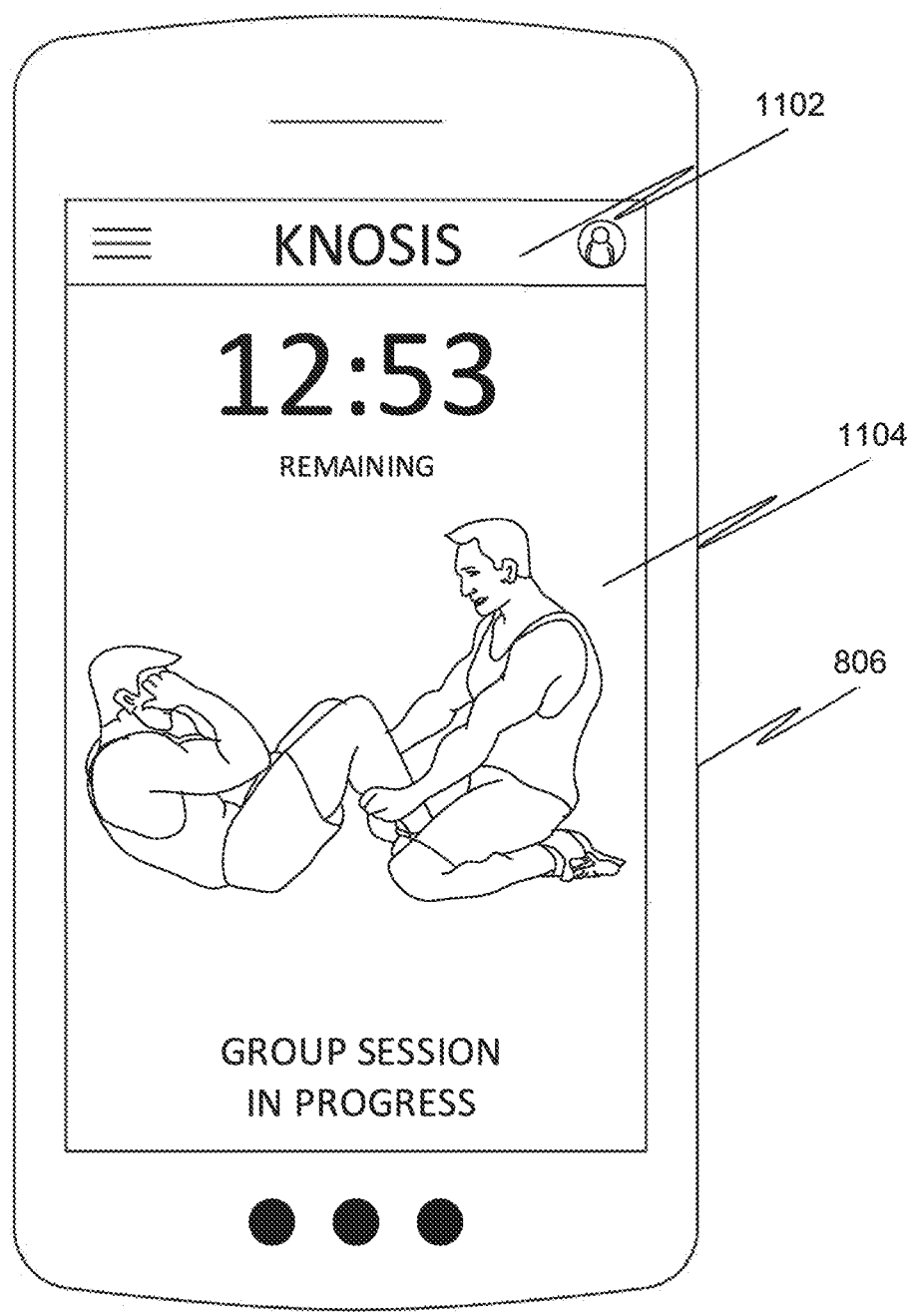
FIG. 11 is a user interface of the mobile application showing a live stream, in accordance with an exemplary embodiment.

As shown in FIG. 11, the user interface 1102 includes a live stream 1104 related to the group session.

In some embodiments, the one or more user devices may include a wearable monitoring device configured to monitor one or more of one or more physiological variables and one or more physical variables of the one or more users. The one or more physiological variables may include one or more of body temperature, heart rate, respiratory rate, blood pressure, blood-oxygen level and blood-insulin level. Further, the one or more physical variables may include one or more of location, distance travelled, speed, acceleration, and number of repetitive actions. For example, the wearable monitoring device may include a fitness tracking band configured to be worn around a wrist of a user.

In some embodiments, the one or more user devices may include a smart exercising device configured to facilitate performance of an exercise. Further, the smart exercising device may include one or more sensors configured to detect at least one exercise data associated with the exercise. Further, the smart exercising device may include a transceiver configured to transmit the at least one exercise data from the at least one sensor to the communication device. For example, the smart exercising device may include a smart treadmill, a smart dumbbell, a smart weight, a smart strength training equipment, a smart exercise ball, a smart resistance band, a smart exercise mat and a smart shoe.

In some embodiments, the one or more user devices may be configured to monitor food intake corresponding to the one or more users. For example, the one or more user devices may include one or more of a smart oven, a smart food processor and a smart refrigerator.

In some embodiments, the at least one user activity data may correspond to at least one user body part of the one or more users. Further, the at least one user body part corresponds to at least one muscle group of the one or more users. Further, the at least one avatar update data corresponds to at least one avatar body part associated with the at least one user body part.

Figure 12B:
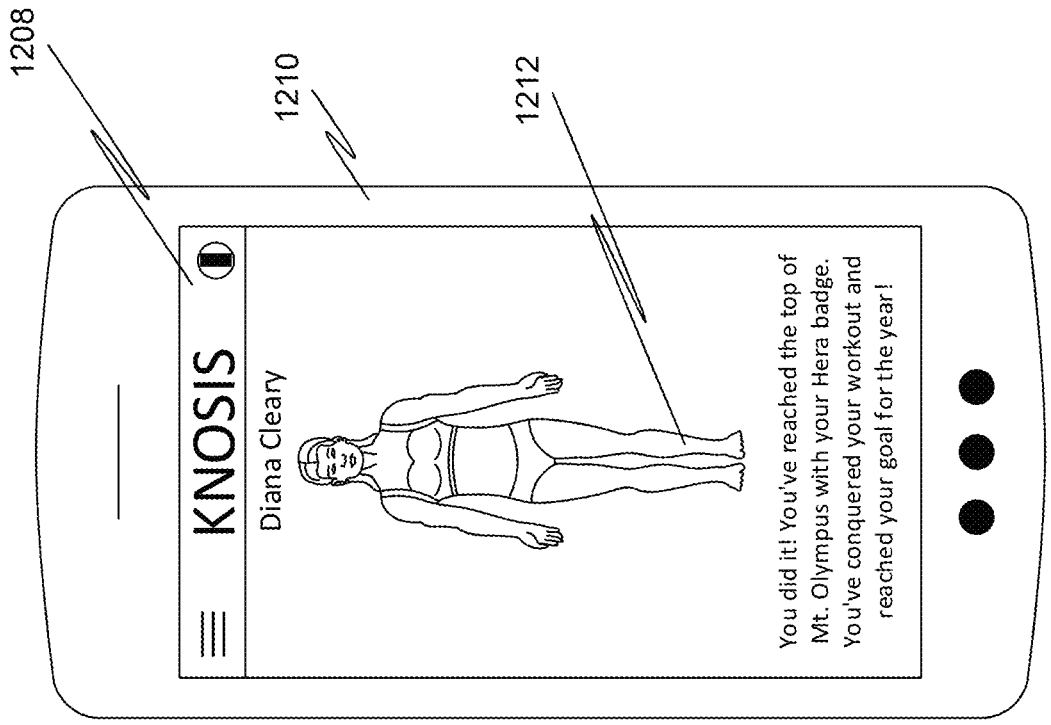
FIG. 12B is a user interface of the mobile application displaying an avatar corresponding to a second user, in accordance with an exemplary embodiment.
Figure 12A:
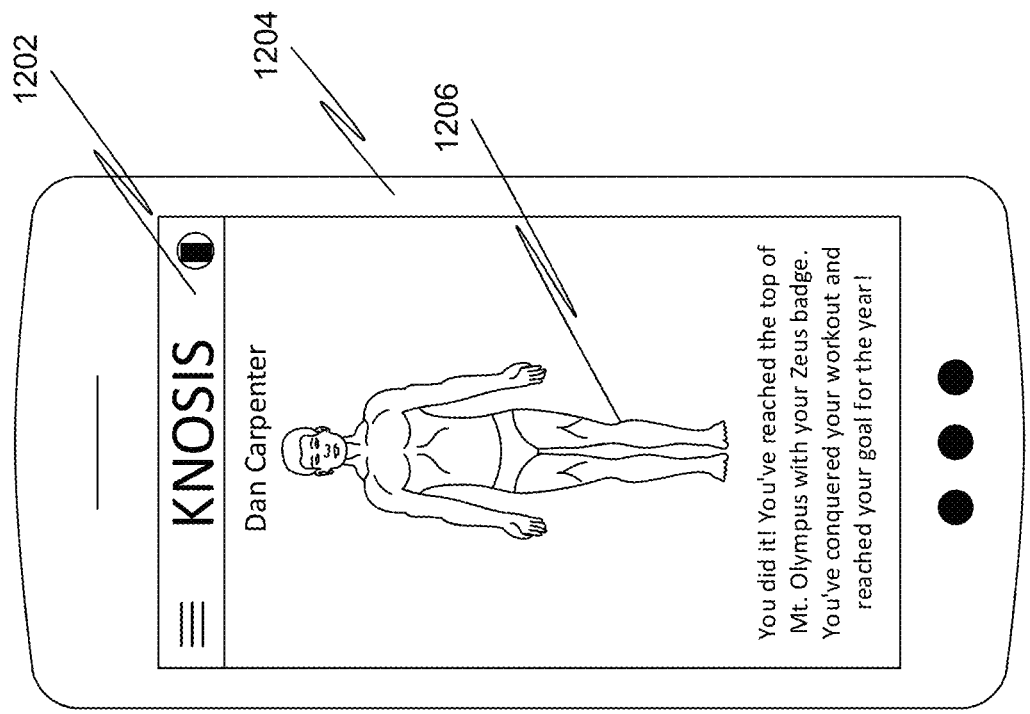
FIG. 12A is a user interface of the mobile displaying an avatar corresponding to a first user, in accordance with an exemplary embodiment.

In further embodiments, the at least one avatar update data may include one or more of fitness improvement data and fitness deterioration data. Further, an appearance of the at least one avatar body part may be based on the at least one avatar update data. FIG. 12A is a user interface 1202 of the mobile application "KNOSIS" installed on a user device 1204 displaying an avatar 1206 corresponding to a first user, in accordance with an exemplary embodiment. The appearance of at least one avatar body part of the avatar 1206 may be based on the at least one avatar update data corresponding to the first user. FIG. 12B is a user interface 1208 of the mobile application "KNOSIS" installed on a user device 1210 displaying an avatar 1212 corresponding to a second user, in accordance with an exemplary embodiment. The appearance of at least one avatar body part of the avatar 1212 may be based on the at least one avatar update data corresponding to the second user.

Figure 13:
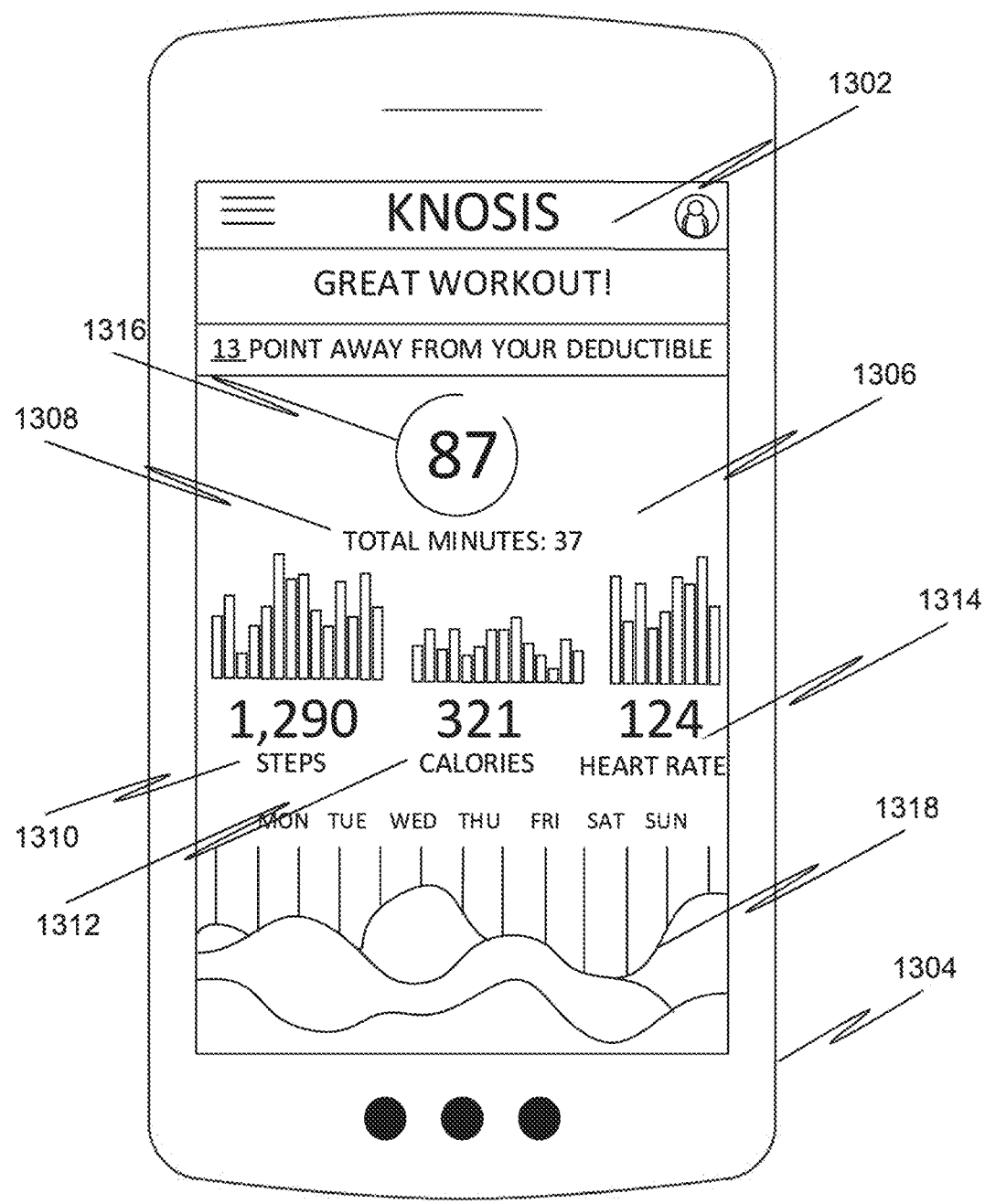
FIG. 13 is a user interface of the mobile application displaying statistics related to a workout performed by a user, in accordance with an exemplary embodiment.

FIG. 13 is a user interface 1302 of the mobile application "KNOSIS" installed on a user device 1304 displaying statistics 1306 related to a workout performed by a user, in accordance with an exemplary embodiment. The workout may be related to a physical health goal of the user. The statistics 1306 may include one or more of a time spent 1308 on the workout, a number of steps 1310 taken by the user, calories burnt 1312, a heart rate 1314 and earned reward points 1316. Further, the statistics 1306 may include one or more graphs 1318 related to the various parameters.

Figure 14:
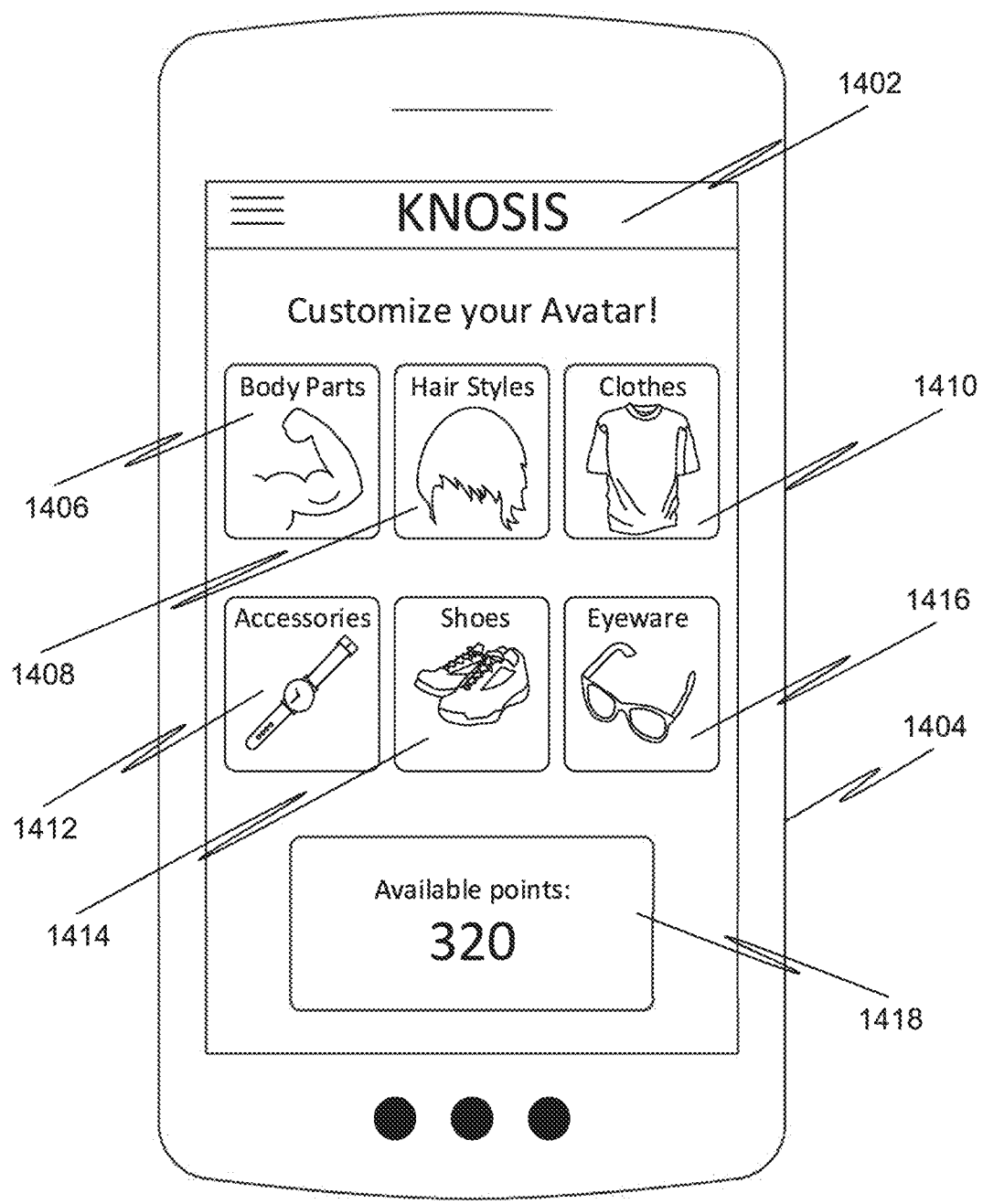
FIG. 14 is a user interface of the mobile application displaying one or more unlocked features, in accordance with an exemplary embodiment.

FIG. 14 is a user interface 1402 of the mobile application "KNOSIS" installed on a user device 1404 displaying one or more unlocked features 1406-1416, in accordance with an exemplary embodiment. The user of the user device 1404 may access the one or more unlocked features 1406-1416 to modify one or more of an avatar body part, an avatar accessory, and an avatar clothing. The one or more features may be locked initially. Then, the one or more of the one or more features may be unlocked as and when the user achieves the one or more wellness goals. The user's achievements may be tracked using reward points. For example, the user interface 1402 shows available reward points 1418.

Figure 15:
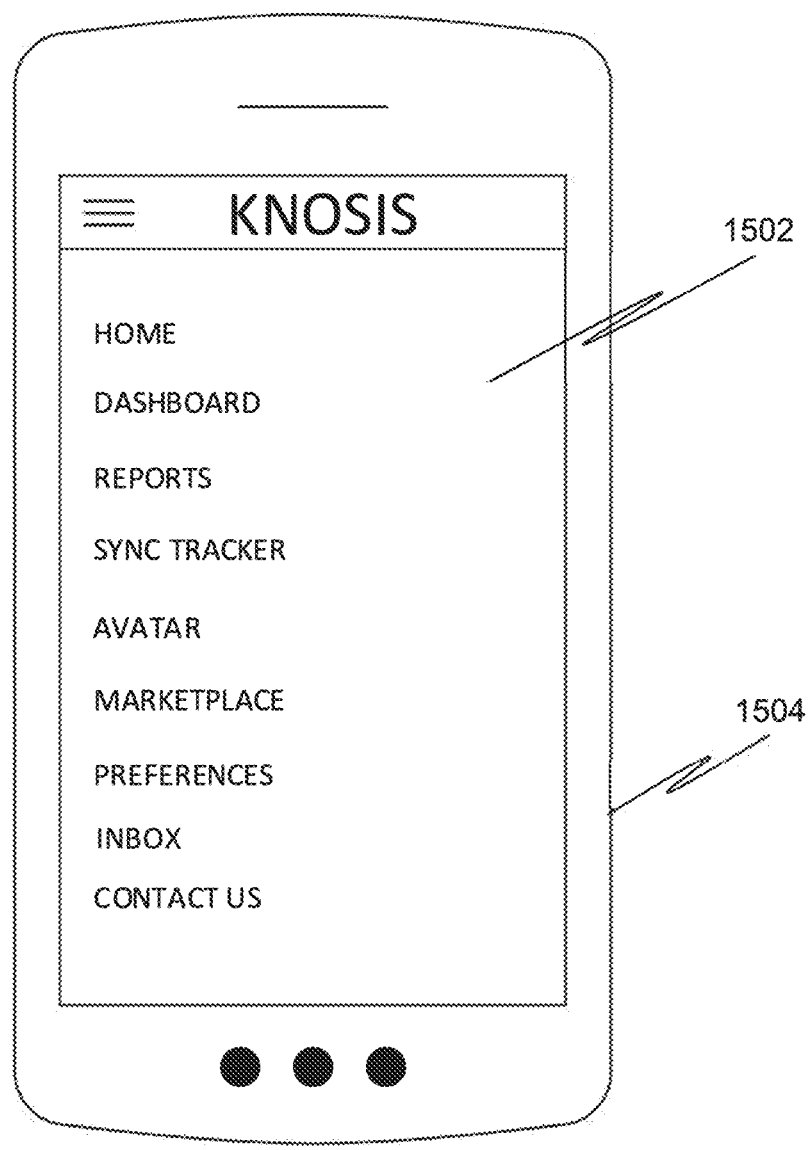
FIG. 15 is a user interface of the mobile application displaying a menu with a list of pages available to a user, in accordance with an exemplary embodiment.

FIG. 15 is a user interface 1502 of the mobile application "KNOSIS" installed on a user device 1504 displaying a menu with a list of pages available to a user, in accordance with an exemplary embodiment. The list of pages may include one or more of a home page, a dashboard page, a reports page, a sync tracker page, an avatar page, a marketplace page, a preferences page, an inbox page and a contact us page. The user may select any page on the user interface 1502, such that the mobile application "KNOSIS" displays the corresponding page. For example, if the user selects the dashboard page, then the mobile application "KNOSIS" displays the dashboard page 1602 shown in FIG. 16.

Figure 16:
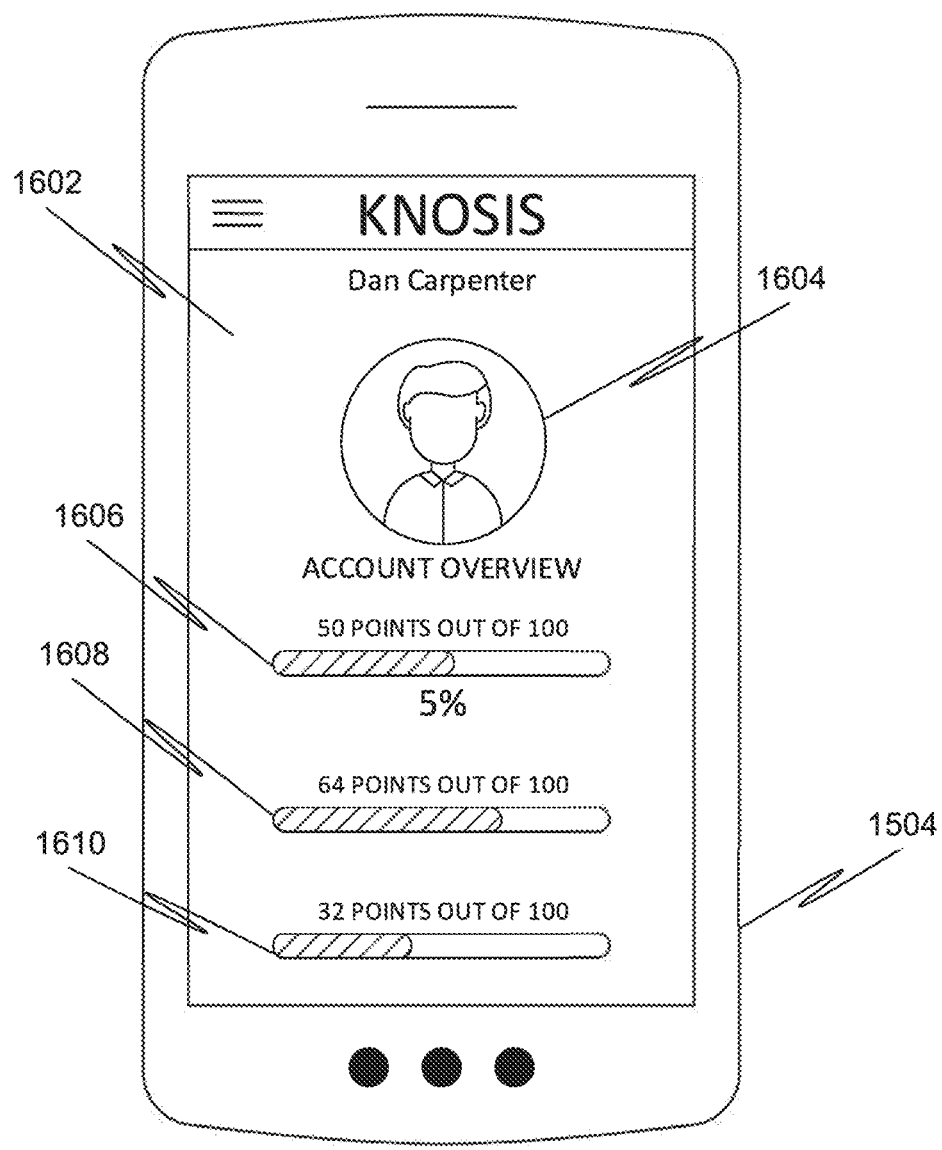
FIG. 16 is a user interface of the mobile application displaying a dashboard page, in accordance with an exemplary embodiment.

As shown in FIG. 16, the dashboard page 1602 may include a profile photo 1604. Further, the dashboard page 1602 may include information about reward points earned by the user. For example, the information about reward points earned by the user may include reward points accumulated for premium discount User Financial Incentive (UFI), reward points accumulated for co-pay UFI and reward points accumulated for deductible UFI. An employer may apply the UFI for the user if the user meets certain monthly Key Performance Indicators (KPIs) based on their activity. Accordingly, the dashboard page 1602 may include a bar 1606 related to the reward points accumulated for premium discount UFI, a bar 1608 related to the reward points accumulated for co-pay UFI and a bar 1610 related to the reward points accumulated for deductible UFI.

Figure 17:
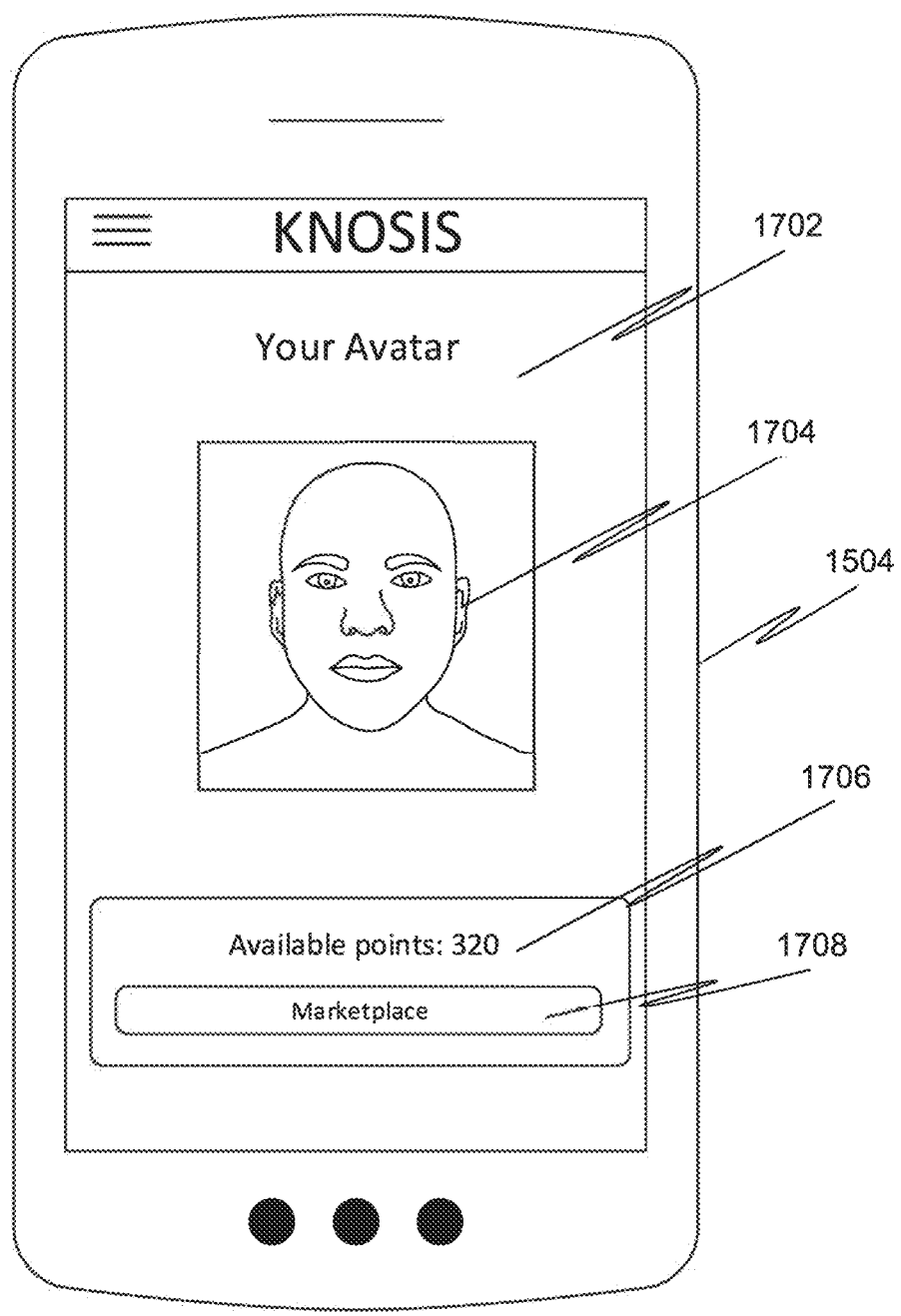
FIG. 17 is a user interface of the mobile application displaying an avatar page, in accordance with an exemplary embodiment.

Further, on the user interface 1502, if the user selects the avatar page, then the mobile application "KNOSIS" displays the avatar page 1702 shown in FIG. 17. The avatar page 1702 includes an avatar 1704 of the user. Further, the avatar page 1702 includes information about the reward points earned 1706. Further, the avatar page 1702 includes a "marketplace" button 1708. When the user selects the "marketplace" button 1708, then the mobile application "KNOSIS" displays the user interface 1402. The user interface 1402 may allow the user to unlock one or more locked features by using the reward points.

Figure 18:
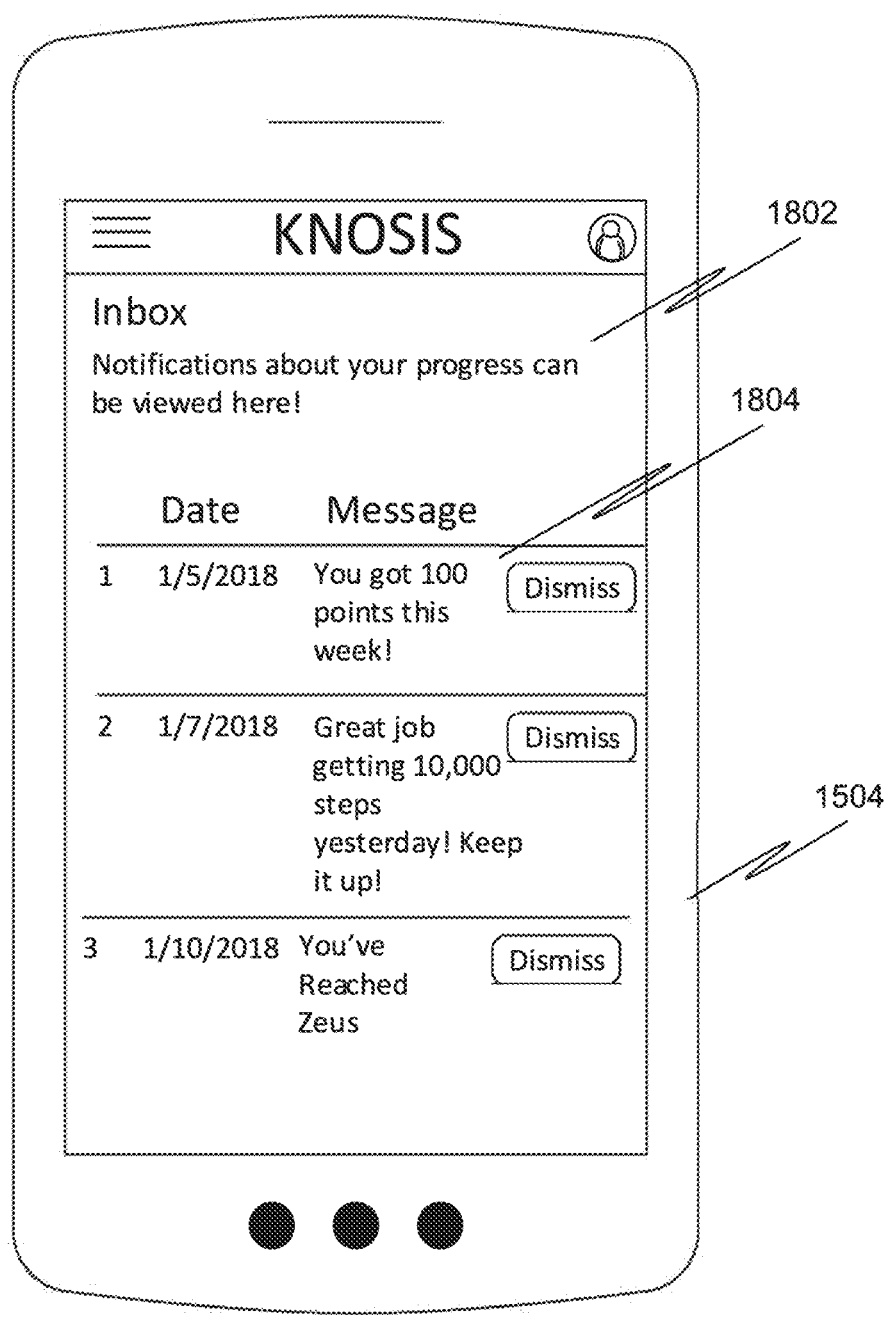
FIG. 18 is a user interface of the mobile application displaying an inbox page, in accordance with an exemplary embodiment.

Further, on the user interface 1502, if the user selects the inbox page, then the mobile application "KNOSIS" displays the inbox page 1802 shown in FIG. 18. The inbox page may show the various notifications 1804 about the progress of the user. Further, the inbox page may show messages containing credits, tokens, coupons, special member pricing, and other incentives of monetary value when they achieve their wellness goals. The messages may be sent by partner businesses, sponsors, and other organizations.

Figure 19:
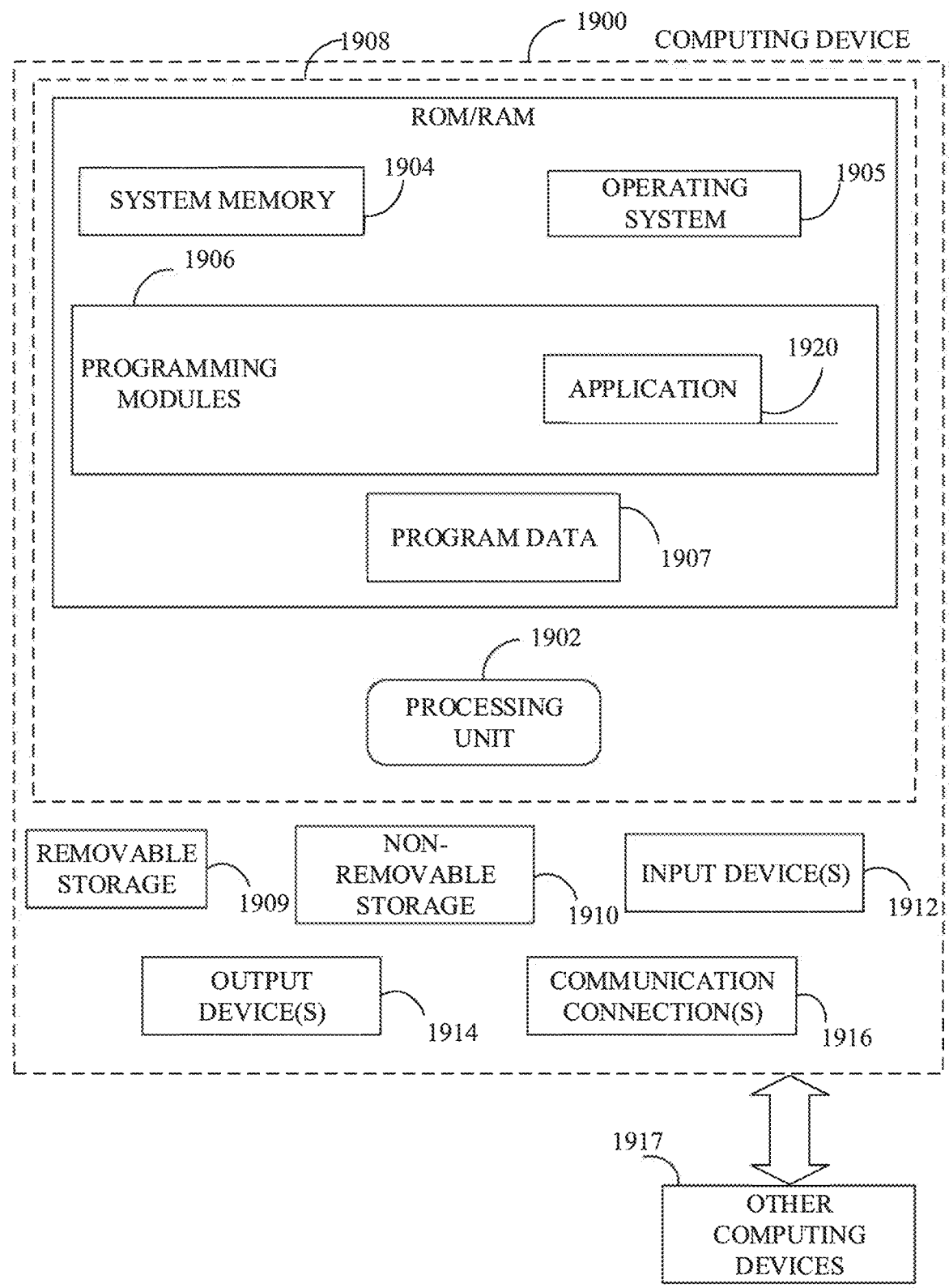
FIG. 19 illustrates an exemplary computing system that may be employed to implement processing functionality for various embodiments.

FIG. 19 is a block diagram of a system including computing device 1900. Consistent with an embodiment of the disclosure, the aforementioned memory storage and processing unit may be implemented in a computing device, such as computing device 1900 of FIG. 19. Any suitable combination of hardware, software, or firmware may be used to implement the memory storage and processing unit. For example, the memory storage and processing unit may be implemented with computing device 1900 or any of other computing devices 1917, in combination with computing device 1900. The aforementioned system, device, and processors are examples and other systems, devices, and processors may comprise the aforementioned memory storage and processing unit, consistent with embodiments of the disclosure.

With reference to FIG. 19, a system consistent with an embodiment of the disclosure may include a computing device or cloud service, such as computing device 1900. In a basic configuration, computing device 1900 may include at least one processing unit 1902 and a system memory 1904. Depending on the configuration and type of computing device, system memory 1904 may comprise, but is not limited to, volatile (e.g. random access memory (RAM)), non-volatile (e.g. read-only memory (ROM)), flash memory, or any combination. System memory 1904 may include operating system 1905, one or more programming modules 1906, and may include a program data 1907. Operating system 1905, for example, may be suitable for controlling computing device 1900's operation. Accordingly, in some embodiments, the programming modules 1906 may be implemented using one or more of software and hardware. For example, in an instance, the programming modules 1906 may be implemented as modules of a Digital Signal Processor (DSP). Further, in another instance, multiple types of completely DSP chip powered and/or analog physical hardware unit designs may be used. Further, the implementation of the programming modules could also be a combination of mostly DSP modules with some analog modules/processing as well. Further, in some embodiments, as long as the dithering module is implemented via a DSP chip, technically the rest of the modules may be analog modules. Accordingly, stress testing may be performed to determine which components would be best for each unit's physical size limitations.

Furthermore, embodiments of the disclosure may be practiced in conjunction with a graphics library, other operating systems, or any other application program and is not limited to any particular application or system. This basic configuration is illustrated in FIG. 19 by those components within a dashed line 1908. Computing device 1900 may have additional features or functionality. For example, computing device 1900 may also include additional data storage devices (removable and/or non-removable) such as, for example, magnetic disks, optical disks, or tape. Such additional storage is illustrated in FIG. 19 by a removable storage 1909 and a non-removable storage 1910. Computer storage media may include volatile and nonvolatile, removable and non-removable media implemented in any method or technology for storage of information, such as computer-readable instructions, data structures, program modules, or other data. System memory 1904, removable storage 1909, and non-removable storage 1910 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1900. Any such computer storage media may be part of device 1900. Computing device 1900 may also have input device(s) 1912 such as a keyboard, a mouse, a pen, a sound input device, a touch input device, etc. Output device(s) 1914 such as a display, speakers, a printer, etc. may also be included. The aforementioned devices are examples and others may be used.

Computing device 1900 may also contain a communication connection 1916 that may allow device 1900 to communicate with other computing devices 1918, such as over a network in a distributed computing environment, for example, an intranet or the Internet. Communication connection 1916 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1904, including operating system 1905. While executing on processing unit 1902, programming modules 1906 (e.g., application 1920) may perform processes including, for example, one or more stages of methods, algorithms, systems, applications, servers, databases as described above. The aforementioned process is an example, and processing unit 1902 may perform other processes.

Figure 20:
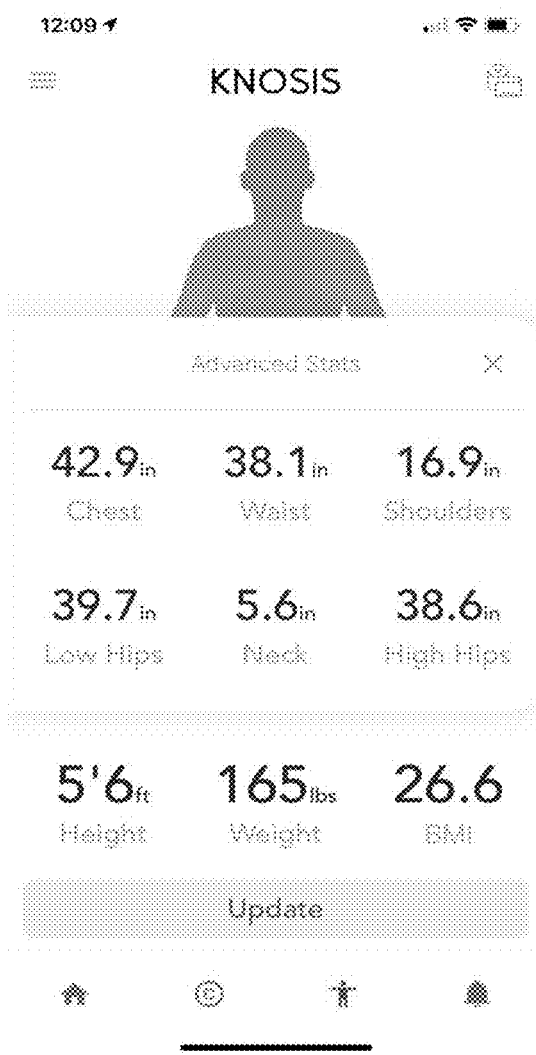
FIGS. 20-22 show the use of artificial intelligence, taking the two full body pictures of the user and generating and providing an avatar along with the user's body measurements.
Figure 21:
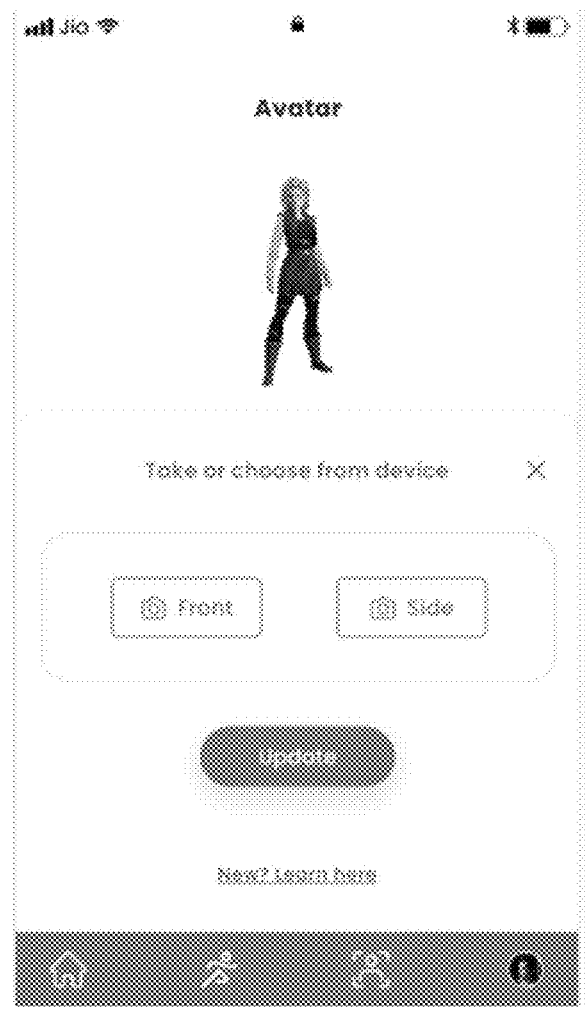
Figure 22:
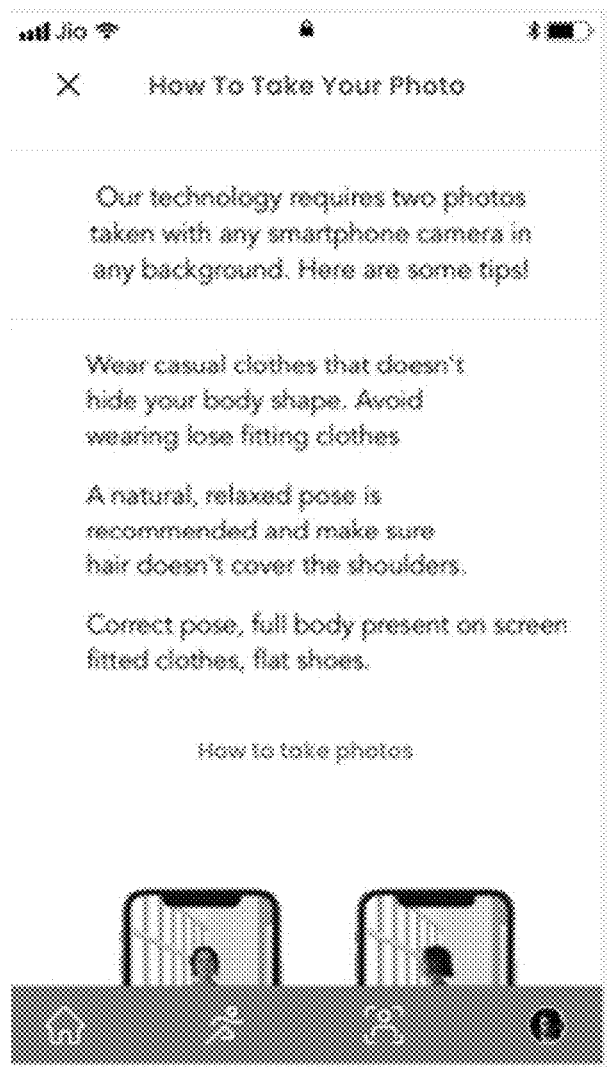
Figure 23:
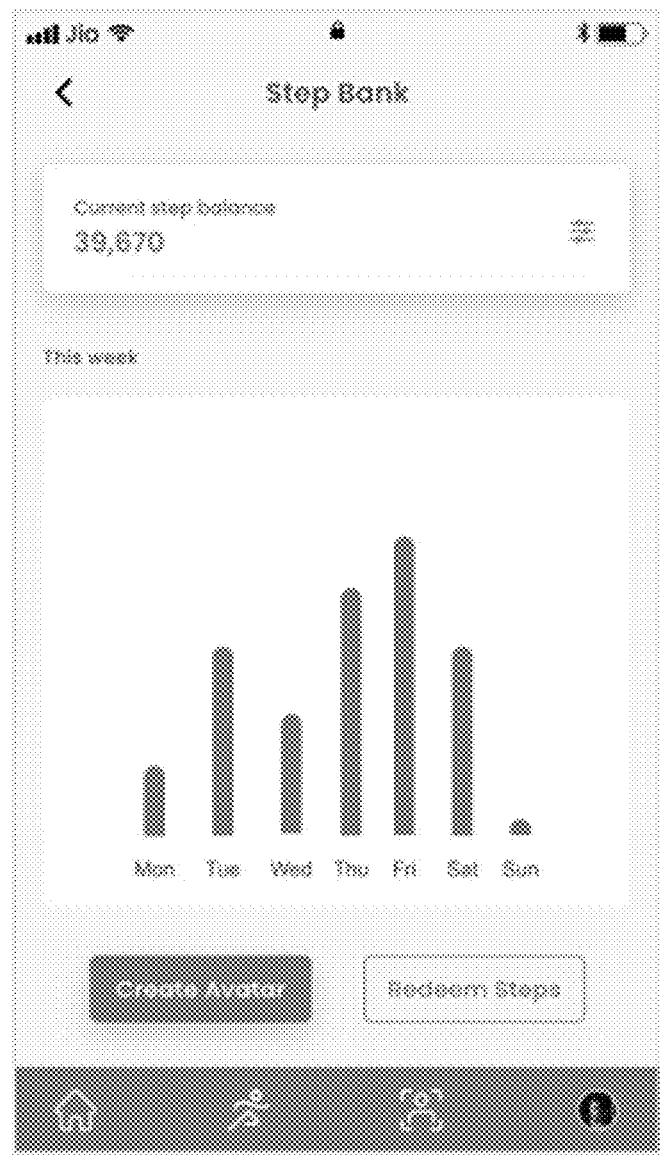
FIGS. 23 & 24 show the use of a "step bank" feature which accumulates the user's steps as they exercise over time and allows them to redeem the steps earned at businesses on a network offering user financial incentive challenges.
Figure 24:
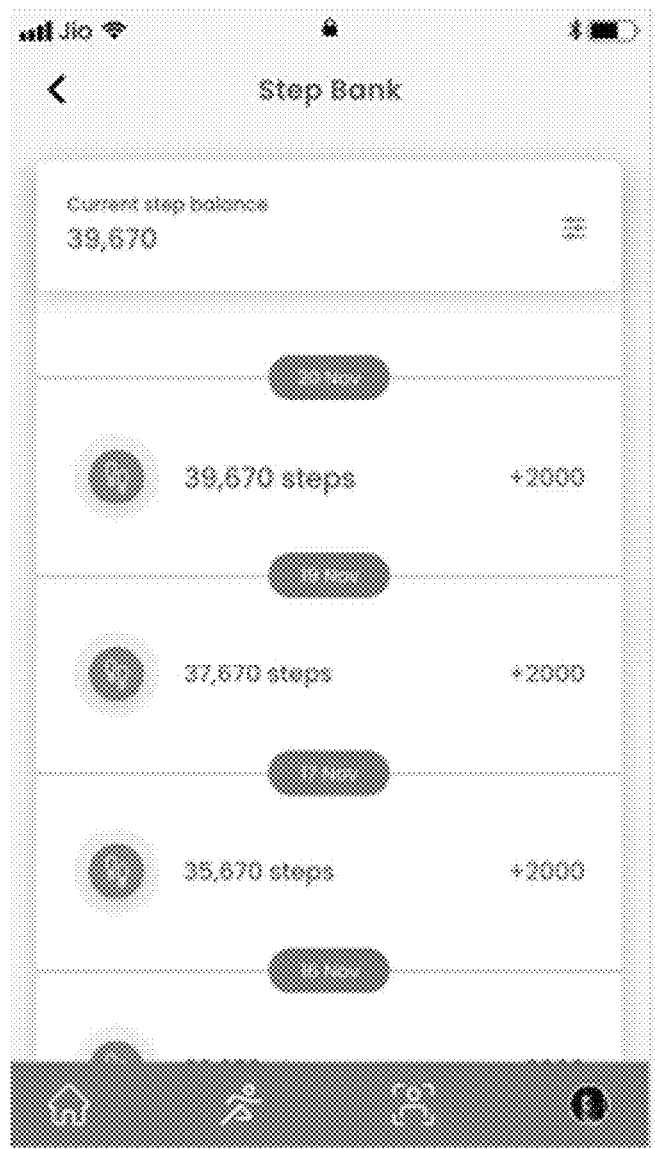
Figure 25:
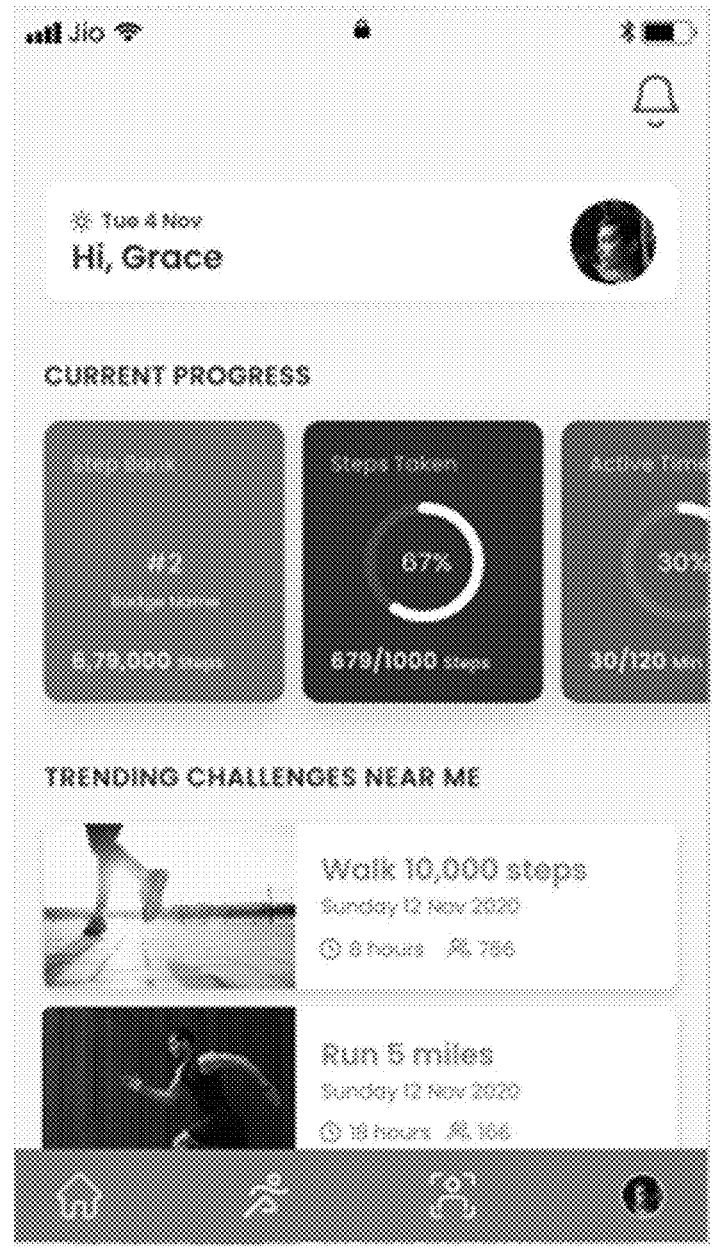
FIG. 25 shows how users can choose from challenges that are trending via a hashtag (#) on the application's dashboard that also shows their stats.
Figure 26:
FIGS. 26-29 show how users can access a map view and a list view of user financial incentive challenges by searching within a given distance radius using location services or by trending hashtags (#).
Figure 27:
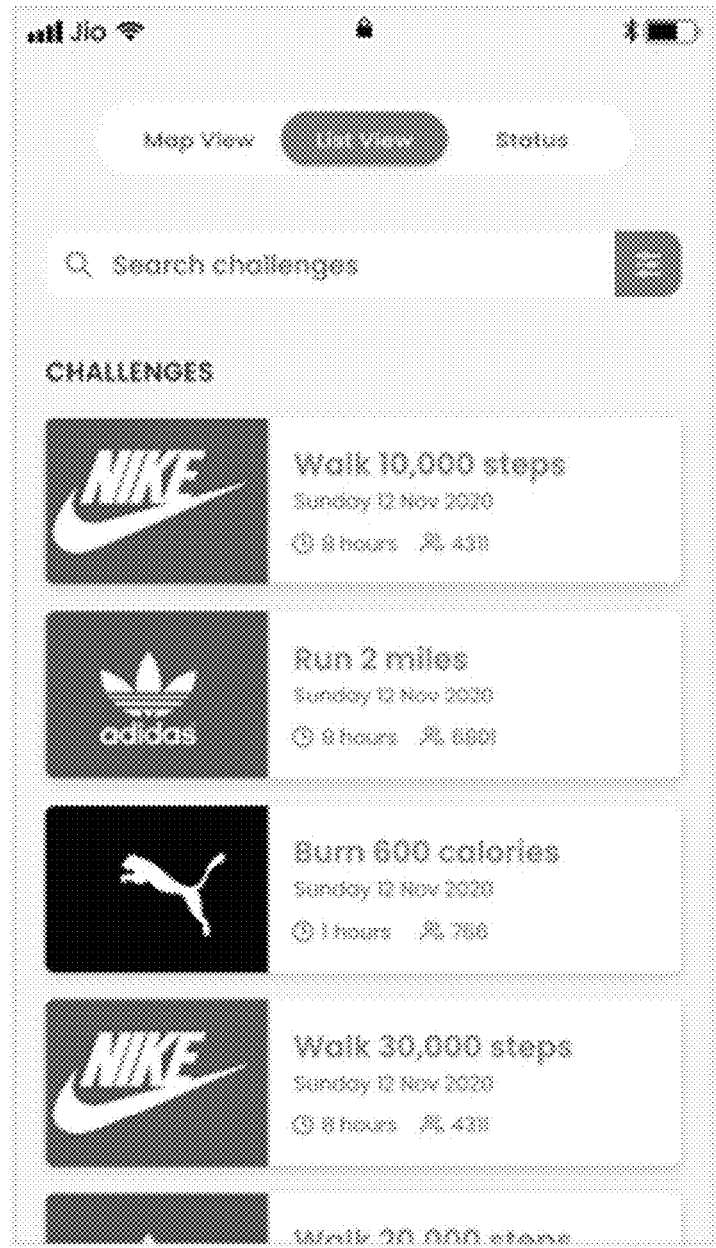
Figure 28:
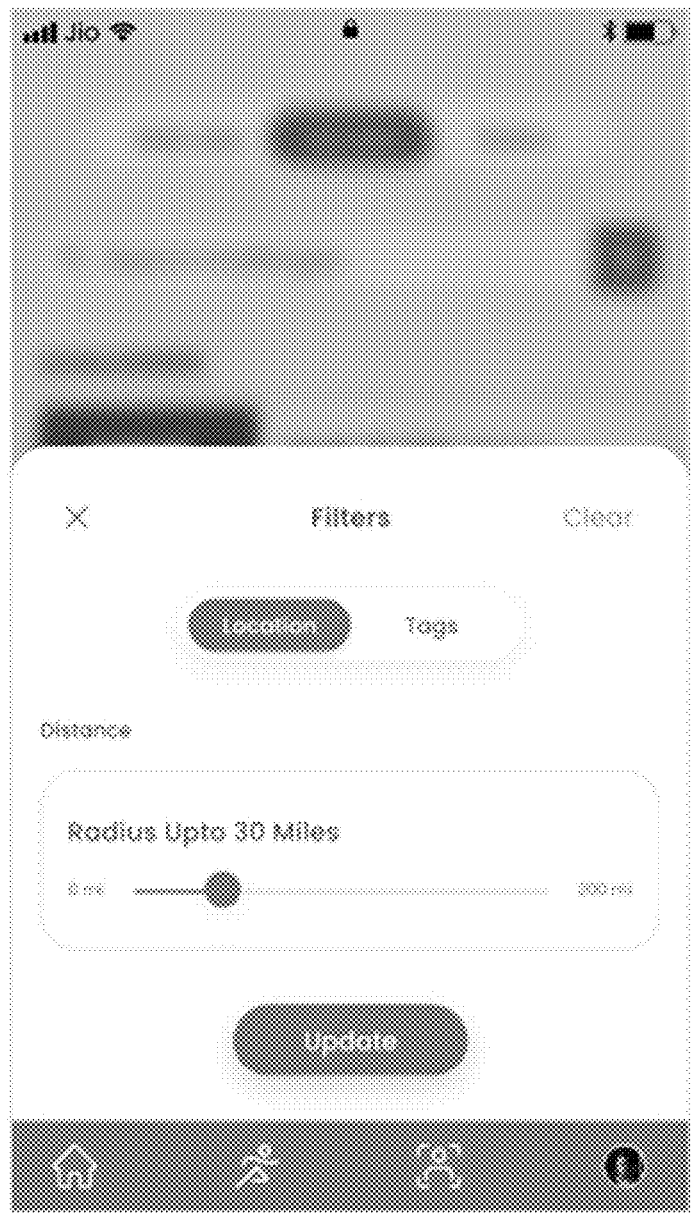
Figure 29:
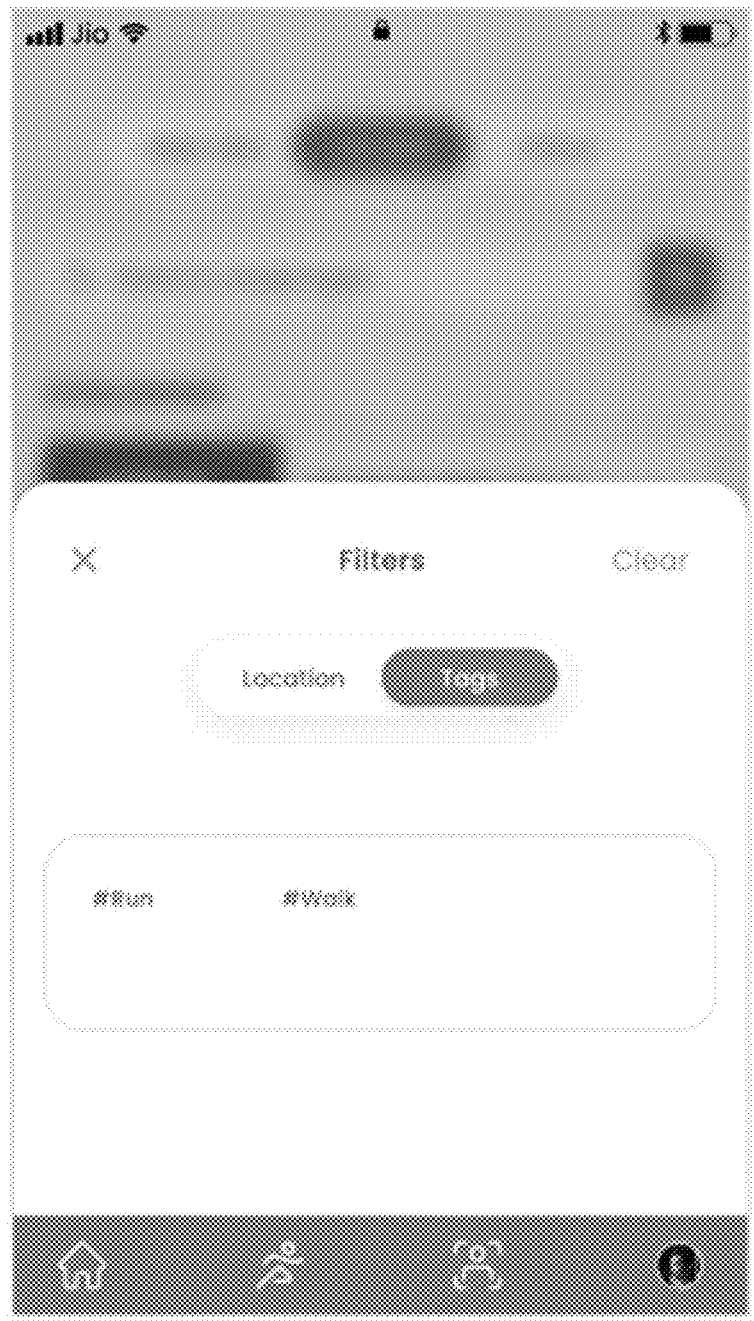
Figure 30:
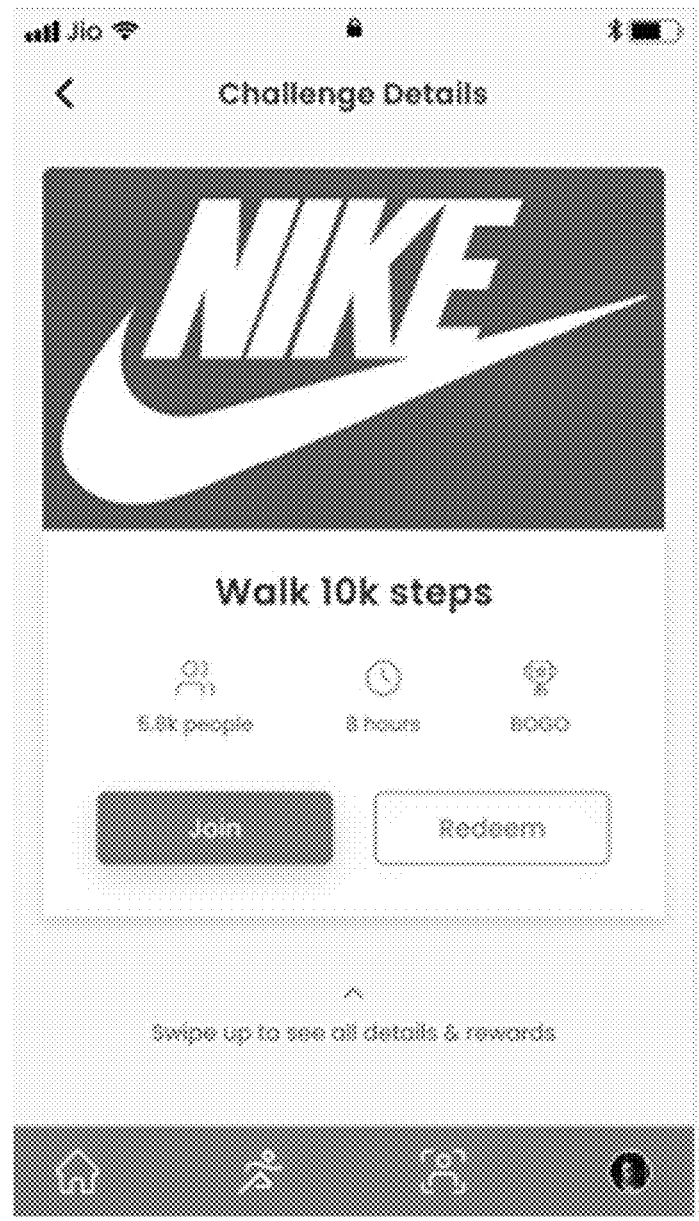
FIG. 30 shows how a user can view the challenge details as well as the UFI offered before choosing to accept or redeem challenge.
Figure 31:
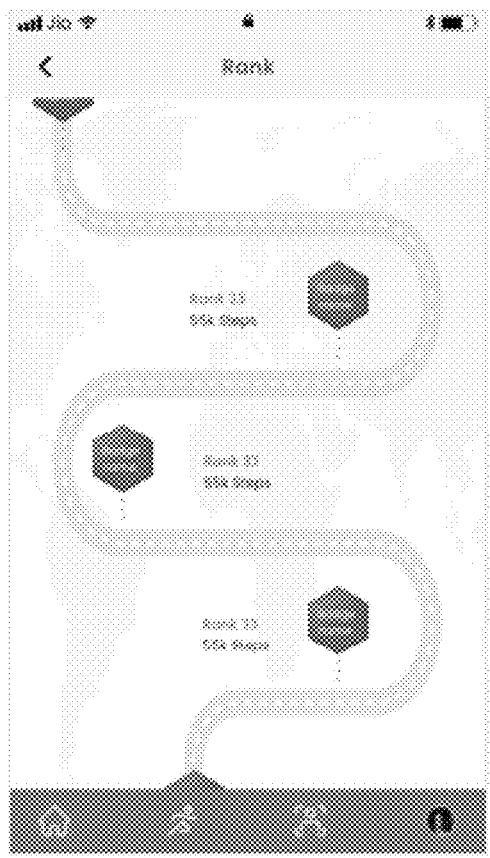
FIGS. 31 & 32 illustrate a ranking system being provided such that users can see their ranking journey.
Figure 32:
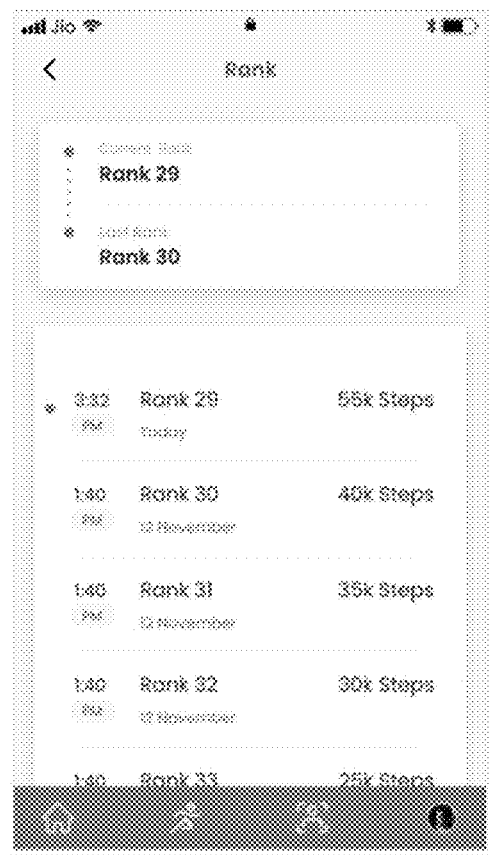
Figure 33:
FIG. 33 shows the use of Augmented Reality (AR) fit finding technology wherein users can go on scavenger hunts for incentives that have been set by partner businesses wherein the amount of exercise time, steps, or distance can unlock various incentives that appear before them using AR.

In an advanced embodiment, as shown in FIGS. 20-29, the method and system of facilitating management of wellness of users includes a "system and method for incentivizing mobile platform users using user financial incentives, challenges, and gamification through partner businesses". This accomplished by the following steps:

1. Using a communication device, for example mobile devices 106 or communication device 202, including a computer therein and incorporating artificial intelligence software encoded thereon and/or within mobile application "KNOSIS", taking two full body pictures of a user, ie., via a camera installed thereon.
2. Using artificial intelligence, taking the two full body pictures of the user and generating and providing an avatar along with the user's body measurements, as shown in FIGS. 20-22.
3. Using a "step bank" feature, encoded upon the computer and/or within mobile application "KNOSIS", with which accumulates the user's steps as they exercise over time and allows them to redeem the steps earned at businesses on a network offering user financial incentive challenges. For example, a business is offering 15% off of a purchase for earning 50$k$ steps within 5 days. Users can use existing steps they have already earned to redeem an incentive/coupon, as shown in FIGS. 23 and 24.
4. Users can choose from challenges that are trending via a hashtag (#) on the application's dashboard that also shows their stats such as: Step Bank/Global Rank, Steps for the Day, and Active Time, as shown in FIG. 25.
5. Users can access a map view and a list view of user financial incentive challenges by searching within a given distance radius using location services or by trending hashtags (#). The challenges display the KPI or challenge criteria as well as incentives, as shown in FIGS. 26-29.
6. User can view the challenge details as well as the UFI offered before choosing to accept or redeem challenge, as shown in FIG. 30.
7. A ranking system is provided such that users can see their ranking journey, as shown in FIGS. 31 and 32.
8. Augmented Reality (AR) fit finding technology is used wherein users can go on scavenger hunts for incentives that have been set by partner businesses wherein the amount of exercise time, steps, or distance can unlock various incentives that appear before them using AR, as shown in FIG. 33, wherein AR soccer balls are collected as they walk through an airport for a prize.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may, in fact, be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

Although the invention has been explained in relation to its preferred embodiment, it is to be understood that many other possible modifications and variations can be made without departing from the spirit and scope of the invention.

What is claimed is:

1. A method of facilitating management of wellness of a user via financial incentives, challenges, and gamification, the method comprising:
    providing a communication device including:
        a computer including artificial intelligence software encoded thereon; and
        a display device;
    providing body measurements of the user to the computer;
    using the communication device to take two images of the user;
    using the artificial intelligence software and body measurements of the user to generate an avatar;
    receiving, using the communication device, at least one wellness goal associated with the user;
    using a step bank feature to accumulate steps of the user over time toward the at least one wellness goal;
    transmitting, using the communication device, the avatar, the at least one wellness goal, and the user's steps to the display device;
    redeeming the user's steps earned at a businesses on a network offering the user the financial incentives, the challenges, and the gamification;
    wherein the financial incentives are based upon meeting certain monthly key performance indicators based on activity of the user toward the at least one wellness goal;
    wherein the monthly key performance indicators are used to earn reward points for the user, and
    wherein the reward points are used by the user to unlock one or more features of the avatar, wherein the one or more features of the avatar comprise body parts, physical features, accessories for the avatar, and customizable portions of the avatar, wherein the customizable portions of the avatar include hair, torso, arms, legs, and clothing.

2. The method of claim 1 further comprising:
choosing from challenges that are trending over internet via a hashtag.

3. The method of claim 1 further comprising:
providing a dashboard upon the display device; and
displaying user statistics upon the dashboard, wherein the statistics include step bank status, a global rank, steps for the day, and activity times.

4. The method of claim 1 further comprising:
providing a map view and a list view upon the display device of user financial incentive challenges offered by using available internet services and searching locations within a given distance radius to the communication device via location services or by trending hashtags.

5. The method of claim 4 further comprising:
providing a ranking system, such that the user can rank journeys and display and see ranking journey.

6. The method of claim 1 further comprising:
providing augmented reality (AR) fit-finding technology, such that the user can go on scavenger hunts for incentives that have been set by the businesses, wherein an amount of exercise time, steps, or distance can unlock various incentives.

* * * * *